US011117925B2

United States Patent
Lorente Bonde-Larsen et al.

(10) Patent No.: US 11,117,925 B2
(45) Date of Patent: *Sep. 14, 2021

(54) METHODS FOR THE PREPARATION OF DEOXYCHOLIC ACID, AND INTERMEDIATES USEFUL IN THE PREPARATION OF DEOXYCHOLIC ACID

(71) Applicant: BIONICE, S.L.U., Valladolid (ES)

(72) Inventors: Antonio Lorente Bonde-Larsen, Valladolid (ES); Ignacio Herraiz Sierra, Valladolid (ES); Yolanda Fernandez Sainz, Valladolid (ES); Jose Luis Barredo Fuente, Valladolid (ES); Alfonso Perez Encabo, Valladolid (ES); Jose Angel Turiel Hernandez, Valladolid (ES)

(73) Assignee: BIONICE, S.L.U., Valladolid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/579,298

(22) PCT Filed: Jun. 6, 2017

(86) PCT No.: PCT/EP2017/063701
§ 371 (c)(1),
(2) Date: Dec. 4, 2017

(87) PCT Pub. No.: WO2017/211820
PCT Pub. Date: Dec. 14, 2017

(65) Prior Publication Data
US 2018/0305395 A1    Oct. 25, 2018

(30) Foreign Application Priority Data

Jun. 6, 2016   (EP) .................................. 16173095

(51) Int. Cl.
*C07J 9/00* (2006.01)
*C07J 31/00* (2006.01)
*C07J 41/00* (2006.01)
*C07J 71/00* (2006.01)

(52) U.S. Cl.
CPC .............. *C07J 9/005* (2013.01); *C07J 9/00* (2013.01); *C07J 41/0061* (2013.01); *C07J 71/0005* (2013.01); *C07J 31/006* (2013.01)

(58) Field of Classification Search
CPC .... C07J 9/005; C07J 41/0061; C07J 71/0005; C07J 31/006; C07J 9/00
See application file for complete search history.

(56) References Cited

U.S. PATENT DOCUMENTS 2,752,369 A    6/1956  Holysz et al.
6,407,085 B1   6/2002  Kief 8,076,156 B1    12/2011  Xiong
2010/0160276 A1  6/2010  Moriarty et al.
2020/0262863 A1  8/2020  Sierra et al.

FOREIGN PATENT DOCUMENTS

| JP | 16-2004307390 A | 11/2004 |
| JP | 25-2013515006 A | 5/2013 |
| WO | 2008/157635 A2 | 12/2008 |
| WO | 2012/021133 A1 | 2/2012 |
| WO | 2012/174229 A2 | 12/2012 |
| WO | 2013/044119 A1 | 3/2013 |
| WO | 2019/081586 A1 | 5/2019 |

OTHER PUBLICATIONS

Wikipedia, Deoxycholic acid, recovered from https://en.wikipedia.org/wiki/Deoxycholic_acid on Mar. 12, 2019, pp. 1-17. (Year: 2019).*
Kutner et al, Organic Process Research & Development, Technical-Scale Homologation of a Cholanic Acid Derivative through the Barton Ester. A Practical Approach to 25-Hydroxy Vitamin D3 and Congeners, 1998, 2, pp. 290-293. (Year: 1998).*
Ahkrem et al, Total Steroid Synthesis, 1970, Plenum Press, New York, pp. i-362. (Year: 1970).*
Zaragoza Dorwald, Side Reactions in Organic Synthesis, 2005, WILEY-VCH Verlag GmbH & Co. KGaA, Weinheim, Preface. p. IX. (Year: 2005).*
International Search Report and Written Opinion for corresponding Application No. PCT/EP2017/063701 (dated Aug. 3, 2017).
Extended European Search Report for corresponding Application No. 161730951-1451 (dated Oct. 21, 2016).
Albrecht et al., "Process for the Microbiological Peoducation of 1,2-dehydrosteroids," Database CA: Chemical Abstracts Service, Accession No. 1989:552150 (abstract).

(Continued)

*Primary Examiner* — Yevgeny Valenrod
*Assistant Examiner* — Blaine G Doletski
(74) *Attorney, Agent, or Firm* — Troutman Pepper Hamilton Sanders LLP (Rochester)

(57) ABSTRACT

The present invention relates to new and improved processes for the preparation of deoxycholic acid (DCA) and pharmaceutically acceptable salts thereof, as well as to novel intermediates useful for the preparation of DCA and pharmaceutically acceptable salts thereof. The starting compounds are steroids, sterols or fermented phytosterols of vegetable origin, being of formula SM:

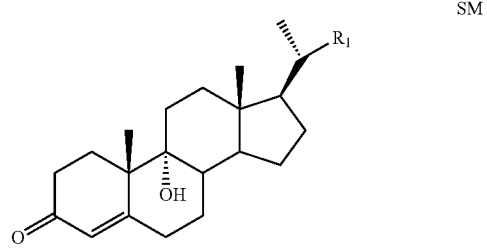

8 Claims, No Drawings

(56) References Cited

OTHER PUBLICATIONS

Yagen et al., "Reduction of the 24,25-double Bond of Lanosterol In vivo in the Rat. Stereochemistry of the Addition of the C-25 Proton in the Biosynthesis of Cholesterol," J. Chem. Soc. Perkin 1:1994-2000 (1974).

Yamada et al., "Mild Oxidation of Aldehydes to the Corresponding Caboxylic Acids and Esters: Alkaline Iodine Oxidation Revisited," Tetrahedron Lett. 33(30:4329-4332 (1992).

Restriction requirement in U.S. Appl. No. 15/831,145 dated Mar. 29, 2019.

Office Action in U.S. Appl. No. 15/831,145, dated Sep. 18, 2019.

CAPLUS printout of U.S. Pat. No. 6,407,085, published Jun. 18, 2002.

Ridlon et al. "Bile Salt Biotransformations by Human Intestinal Bacteria," J. Lipid Res. 47:241-259 (2006).

Office Action in U.S. Appl. No. 15/831,145, dated May 29, 2020.

D. W. Nes, "Biosynthesis of Cholesterol and Other Sterols," Chem. Rev. 111:6423-6451 (2011).

Zhou & Hylemon, "Bile Acids are Nutrient Signaling Hormones," Steroids 86:62-68, 65 (2014).

International Search Report and Written Opinion for corresponding Application No. PCT/EP2018/079173 (dated Jan. 22, 2019).

International Preliminary Report on Patentability for corresponding Application No. PCT/EP2018/079173, dated Jan. 23, 2020.

Cornet et al., "Characterization of the Photosynthetic Pathway of Some Tropical Food Yams (*Dioscorea* spp.) Using Leaf Natural 13 C Abundance," Photosynthetica, 45(2):303-305 (2007).

Hachey et al., "Syntheses with Stable Isotopes: Synthesis of Deuterium and 13 C Labeled Bile Acids", Journal of Labeled Compounds 9(4):703-719 (1973).

Extended European Search Report for co-pending European U.S. Appl. No. 17/198,074, dated Apr. 10, 2018.

Office Action in co-pending European Patent Application No. 17727606.0-1109, dated Jun. 5, 2020.

Office Action for JP 2018-564958 and translation (dated Apr. 13, 2021).

\* cited by examiner

METHODS FOR THE PREPARATION OF DEOXYCHOLIC ACID, AND INTERMEDIATES USEFUL IN THE PREPARATION OF DEOXYCHOLIC ACID

This application is a national stage application under 35 U.S.C. § 371 from PCT Application No. PCT/EP2017/063701, filed Jun. 6, 2017, which claims the benefit of European Patent Application Serial No. 16173095.7, filed Jun. 6, 2016, which is hereby incorporated by reference in its entirety.

FIELD OF THE INVENTION

The present invention relates to new and improved processes for the preparation of deoxycholic acid (DCA) and pharmaceutically acceptable salts thereof, as well as to novel intermediates useful for the preparation of DCA and pharmaceutically acceptable salts thereof.

BACKGROUND OF THE INVENTION

Deoxycholic acid (DCA) is a known drug compound. DCA has the CAS number [83-44-3], and is also known as deoxycholate, cholanoic acid, and 3α,12β-dihydroxy-5β-cholanate. Pure DCA is a white to off-white crystalline powder.

DCA is one of the secondary bile acids, which are metabolic byproducts of intestinal bacteria.

Since its discovery DCA has been used in various fields of human medicine. In the human body DCA is used in the emulsification of fats for the absorption in the intestine. Also, when injected into submental fat, DCA helps destroying fat cells. In the United States DCA has been approved by the Food and Drug Administration (FDA) for reducing moderate-to-severe fat below the chin, and is marketed under the trademark Kybella®. Kybella® is produced by Kythera Biopharmaceuticals.

Recent patent applications describing DCAs fat-reducing properties include WO 2005/117900, WO 2005/112942, US 2005/0261258, US 2005/0267080, US 2006/127468 and US 2006/0154906.

Pharmaceutical preparations containing bile acids are commercially available at rather low costs, because bile acids are easily available from animal corpses, such as cows and sheep.

However, bile acids obtained from animal sources may contain pathogens, such as prions, or other harmful agents, such as toxins.

Bile acids from animal sources are typically purified in order to exclude impurities. In practice such purified compositions contain a mixture of bile acids. For example, commercially available compositions of DCA of animal origin contain some chenodoxycholic acid and cholic acid.

Accordingly, bile acids, including DCA, obtained either synthetically or from plant sources, have recently gained increased interest since the above-mentioned problems associated with bile acids from animal origin can thereby be eliminated.

Thus, there is a need for novel and efficient synthetic routes for preparing bile acids, including DCA, where the starting compounds are steroids, sterols or fermented phytosterols of vegetable origin.

It is known to prepare DCA starting from phytosterols obtained by fermentation of a *Mycobacterium* strain. For example, WO 2008/157635 and WO 2013/044119 describe the synthesis of DCA from 9-hydroxy-4-androstene-3,17-dione:

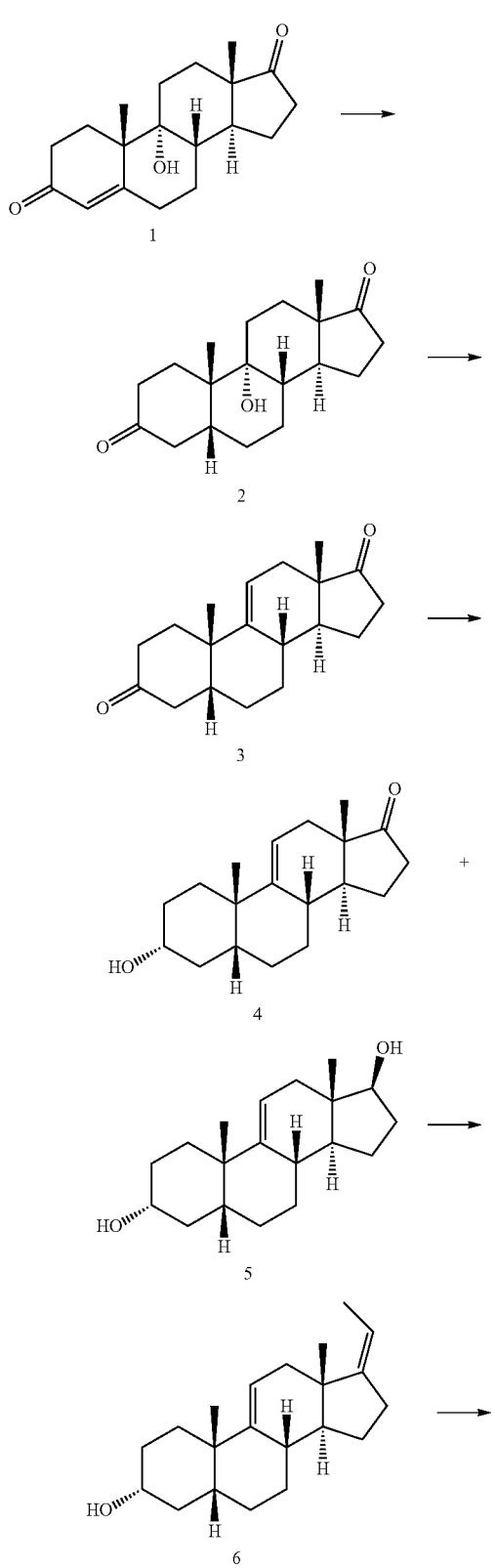

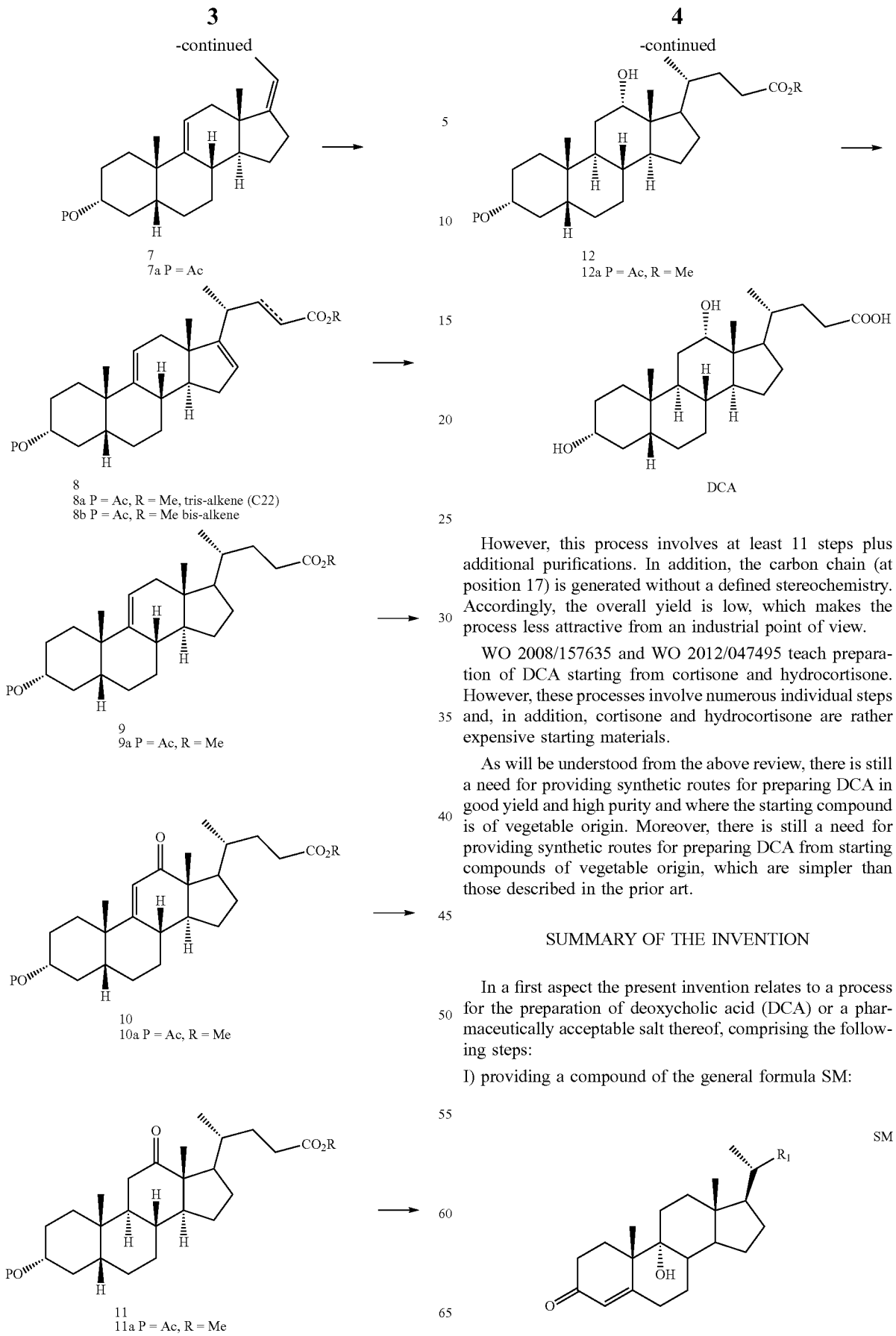

However, this process involves at least 11 steps plus additional purifications. In addition, the carbon chain (at position 17) is generated without a defined stereochemistry. Accordingly, the overall yield is low, which makes the process less attractive from an industrial point of view.

WO 2008/157635 and WO 2012/047495 teach preparation of DCA starting from cortisone and hydrocortisone. However, these processes involve numerous individual steps and, in addition, cortisone and hydrocortisone are rather expensive starting materials.

As will be understood from the above review, there is still a need for providing synthetic routes for preparing DCA in good yield and high purity and where the starting compound is of vegetable origin. Moreover, there is still a need for providing synthetic routes for preparing DCA from starting compounds of vegetable origin, which are simpler than those described in the prior art.

SUMMARY OF THE INVENTION

In a first aspect the present invention relates to a process for the preparation of deoxycholic acid (DCA) or a pharmaceutically acceptable salt thereof, comprising the following steps:

I) providing a compound of the general formula SM:

II) reducing the compound of the general formula SM to obtain an intermediate of the general formula INT 1:

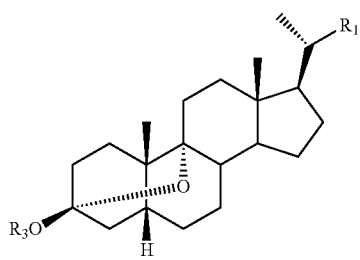

INT 1

III) converting the intermediate of the general formula INT 1 into an intermediate of the general formula INT 2:

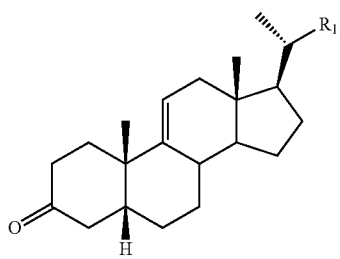

INT 2

IVa) reducing the intermediate of the general formula INT 2 into an intermediate of the general formula INT 3:

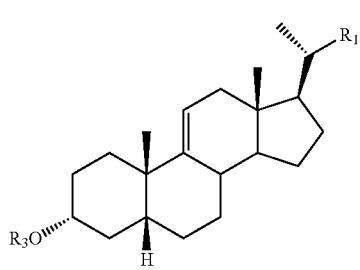

INT 3 followed by converting the intermediate of the general formula INT 3 into an intermediate of the general formula INT B:

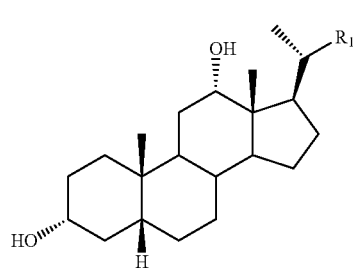

INT B or

IVb) converting the intermediate of the general formula INT 2 into an intermediate with the general formula INT B:

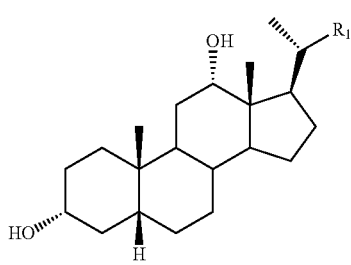

INT B

V) converting the intermediate of the general formula INT B into deoxycholic acid (DCA):

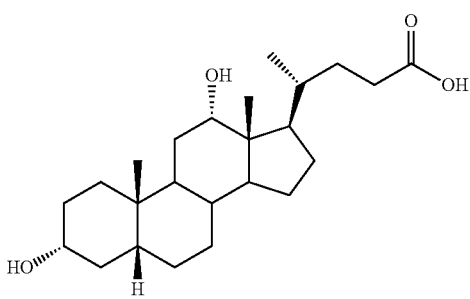

DCA

VI) optionally converting deoxycholic acid to a pharmaceutically acceptable salt thereof,
wherein
$R_1$ is $COOR_2$, $CH_2OH$, $CH_2OP$, $CH_2X$, $CH_2CHO$, $CH_2$—$CH_2$—$OH$, $CH_2$—$CH_2OP$, or $CH_2$—$CH_2X$ or $CH_2$—$CH_2$—$CHO$;
$R_2$ is H or a linear or branched $C_1$-$C_6$-alkyl group;
P is an alcohol protection group;
$R_3$ either P or $R_2$; and
X is a halogen atom.

In one embodiment step IVa) is carried out, and step IVb) is not carried out. In another embodiment step IVb) is carried out, and step IVa) is not carried out.

In another aspect the present invention relates to a process for the preparation of deoxycholic acid (DCA) or a pharmaceutically acceptable salt thereof, comprising the following steps:

I) providing a compound of the general formula INT 3:

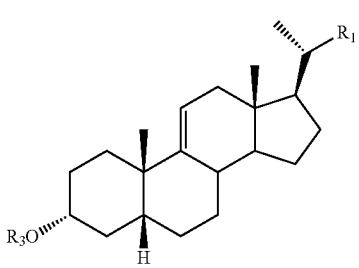

INT 3

II) converting the intermediate of the general formula INT 3 into an intermediate of the general formula INT B:

INT B

III) converting the intermediate of the general formula INT B into deoxycholic acid (DCA):

DCA

IV) optionally converting deoxycholic acid to a pharmaceutically acceptable salt thereof,
wherein
$R_1$ is $COOR_2$, $CH_2OH$, $CH_2OP$, $CH_2X$, $CH_2CHO$, $CH_2—CH_2—OH$, $CH_2—CH_2OP$, or $CH_2—CH_2X$ or $CH_2—CH_2—CHO$;
$R_2$ is H or a linear or branched $C_1$-$C_6$-alkyl group;
P is an alcohol protection group;
$R_3$ either P or $R_2$; and
X is a halogen atom.

In another aspect the present invention relates to a compound of the general formula I

I wherein
$R_1$ is $COOR_2$, $CH_2OP$, $CH_2X$, $CH_2CHO$, $CH_2—CH_2—OH$, $CH_2—CH_2OP$ or $CH_2—CH_2X$;
$R_2$ is H or a linear or branched $C_1$-$C_6$-alkyl group;
P is an alcohol protection group with the proviso that P is not Ac or Pv;

X is a halogen atom;
------ is either a C—C bond or a C=C bond;
⌇⌇⌇ is either =O or ·······OR$_3$ where $R_3$ is either P or $R_2$;
$OR_4$ is either OH or $R_4$ is the $C_3$ carbon in the A ring; and
with the proviso that formula I is not Wherein R is H or Me Wherein R is H or Me In a still further aspect the present invention relates to the use of a compound the general formula I

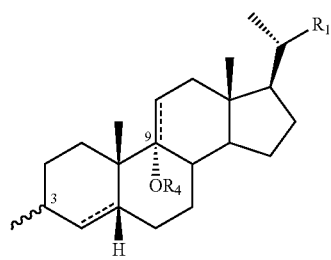

wherein
$R_1$ is $COOR_2$, $CH_2OH$, $CH_2OP$, $CH_2X$, $CH_2CHO$, $CH_2—CH_2—OH$, $CH_2—CH_2OP$, $CH_2—CH_2X$ or $CH_2—CH_2—CHO$;
$R_2$ is H or a linear or branched $C_1$-$C_6$-alkyl group;
P is an alcohol protection group;
X is a halogen atom;
----- either a C—C bond or a C=C bond;
∿∿∿ is either =O or ········ $OR_3$ where $R_3$ is either P or $R_2$; and
$OR_4$ is either OH or $R_4$ is the $C_3$ carbon in the A ring;
for the preparation of a compound of the general formula II or a pharmaceutically acceptable salt thereof.

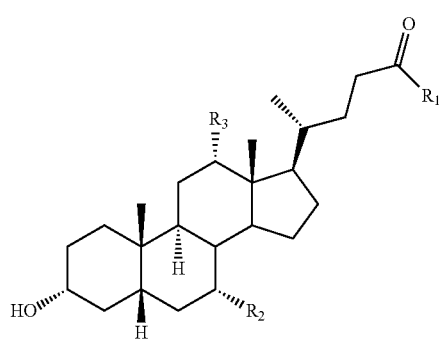

wherein
$R_1$ is OH, $NHCH_2CH_2SO_3H$ or $NHCH_2COOH$;
$R_2$ and $R_3$ is H or OH.

DETAILED DESCRIPTION OF THE INVENTION

Definitions

In the present context the compound of the general formula I is to be understood as either a compound of formula Ia or Ib as shown below.

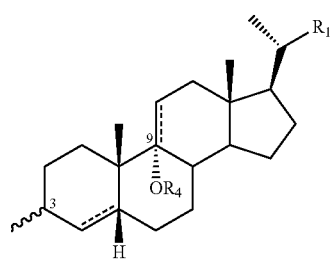

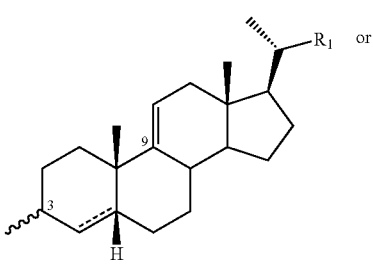

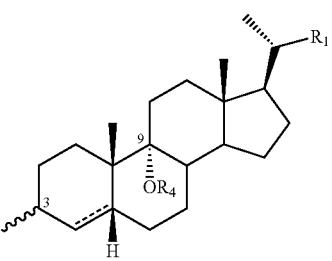

In the present context, the term "$C_1$-$C_6$-alkyl group" is intended to mean a linear or branched saturated carbon chain having from 1 to 6 carbon atoms. Specific examples of a $C_1$-$C_6$-alkyl group are methyl, ethyl, n-propyl, isopropyl, n-butyl, isobutyl, tert-butyl, n-pentyl, isopentyl, n-hexyl and iso-hexyl. Preferred examples include methyl, ethyl, n-propyl and isopropyl, in particular methyl and ethyl. Most preferably, the $C_1$-$C_6$-alkyl group is methyl.

Herein, the term "$C_1$-$C_6$-alkanol" means a linear or branched saturated alcohol having from 1 to 6 carbon atoms.

Specific examples of a $C_1$-$C_6$-alkanol are methanol, ethanol, n-propanol, isopropanol, n-butanol, isobutanol, tert-butanol, n-pentanol, isopentanol, n-hexanol and iso-hexanol. Preferred examples includes methanol, ethanol, n-propanol and isopropanol, in particular methanol and ethanol. Most preferably, the $C_1$-$C_6$-alkanol is methanol.

The term "leaving group" is intended to mean a molecular fragment that is capable of departing from a molecule with a pair of electrons in heterolytic bond cleavage. Specific examples of leaving groups include halides, such a chloride, bromide and iodide, and sulfonate esters, such as tosylate. In a preferred embodiment of the invention the leaving group is bromide.

When used herein, the term "alcohol protection group" means a molecule that can modify, and hence temporarily mask the characteristic chemistry of, an alcohol group. Specific examples of alcohol protection groups include trimethylsilyl ether (TMS), triethylsilyl ether (TES), triisopropylsilyl ether (TIPS), tert-butyldimethylsilyl ether (TBS, TBDMS), tert-butyldiphenylsilyl ether (TBDPS), acetyl (Ac, $COCH_3$), benzoyl (Bz), benzyl ether (Bn), 4-methoxybenzyl ether (PMB), 2-naphthylmethyl ether (Nap), methoxymethyl acetal (MOM), 2-methoxyethoxy-methyl ether (MEM), ethoxyethyl acetal (EE), methoxypropyl acetal (MOP), benzyloxymethyl acetal (BOM), tetrahydropyranyl acetal (THP), 2,2,2-trichloro-ethyl carbonate (Troc), methyl ether, dimethoxytrityl (DMT), methoxytrityl (MMT), methylthiomethyl ether, pivaloyl (Piv), tetrahydropyranyl (THP), triphenylmethyl (trityl, Tr), and tosyl (Ts) In a preferred embodiment of the invention the alcohol protection group is Ac, TBDMS and Ts, in particular Ac.

In the present context "Ac" means acetyl ($COCH_3$).

A "pharmaceutically acceptable salt" means that the salt is non-toxic and suitable for being administered to a mammal, in particular a human being. Examples of pharmaceutically acceptable salts include salts with a base, e.g. salts with an inorganic base, such as a sodium salt, a potassium salt, a calcium salt, a magnesium salt and the like, or salts with an organic base, such as a piperidine salt, a morpholine salt, a pyrrolidone salt, an arginine salt, a lysine salt and the like. In a preferred embodiment of the invention, the pharmaceutically acceptable salt is the sodium salt.

The Synthetic Routes to DCA

The present inventors have provided new synthetic routes to DCA, which may be described by the following overall reaction scheme:

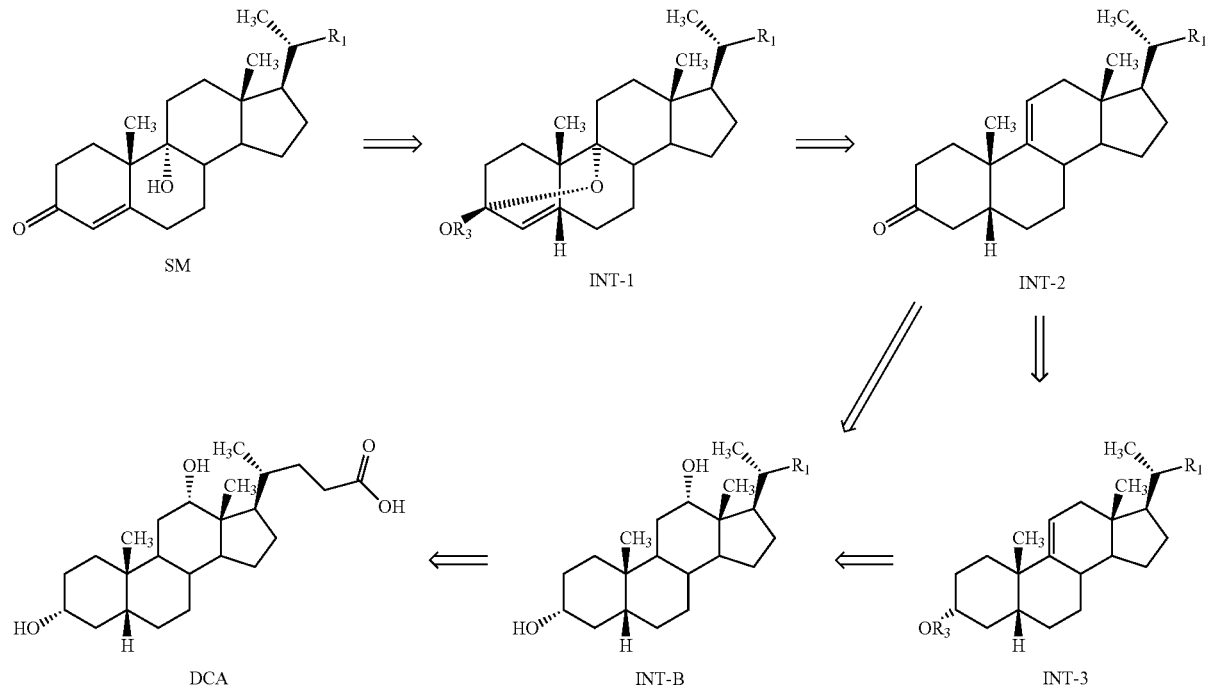

wherein $R_1$ and $R_3$ are as defined previously.

The individual process steps are disclosed in more detail infra.

Synthetic Route A

In a preferred embodiment of the invention, the process for the preparation of deoxycholic acid (DCA) or a pharmaceutically acceptable salt thereof, comprises the following steps:

i) providing a compound of the general formula SM-a:

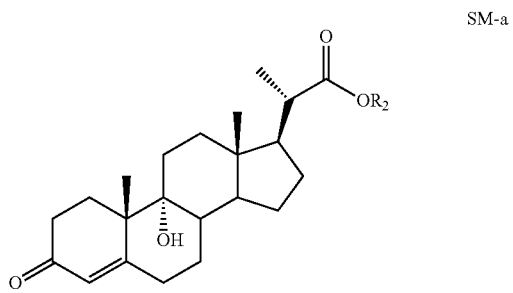

ii) reducing the compound of the general formula SM-a to obtain an intermediate of the general formula Int A1:

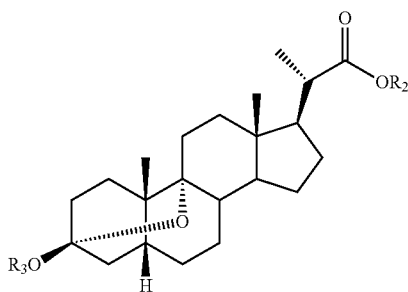

INT A1 iii) converting the intermediate of the general formula Int A1 into an intermediate of the general formula Int A2:

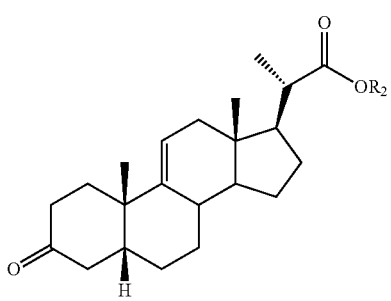

INT A2 iv) reducing the intermediate of the general formula Int A2 into an intermediate of the general formula Int A3:

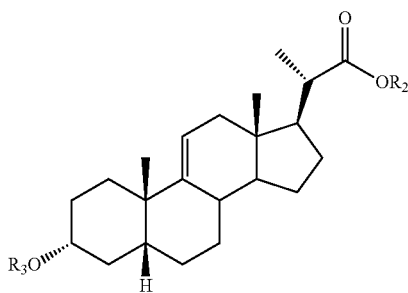

INT A3 v) oxidising the intermediate of the general formula Int A3 into an intermediate of the general formula Int A5:

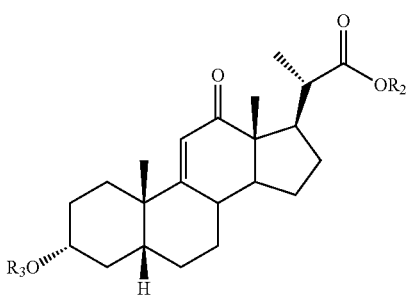

Int A5 vi) reducing the intermediate of the general formula Int A5 into an intermediate of the general formula Int A6:

Int A6 vii) reducing the intermediate of the general formula Int A6 into an intermediate of the general formula Int A7:

Int A7 viii) reducing the compound of the general formula Int A7 into an intermediate of the general formula Int A8:

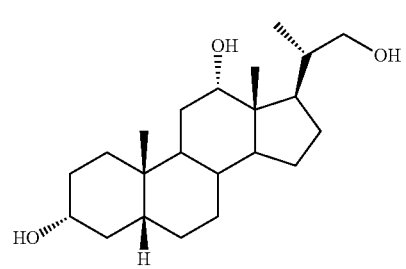

Int A8 ix) elongating the carbon chain of the compound of the general formula Int A8 to obtain deoxycholic acid (DCA):

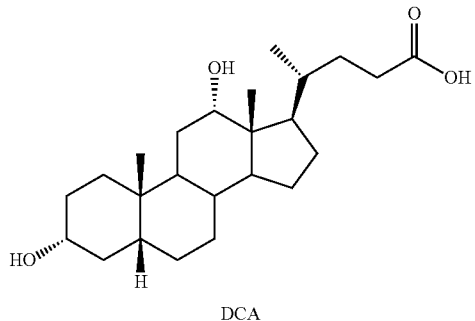

DCA x) optionally converting deoxycholic acid to a pharmaceutically acceptable salt thereof, wherein R$_2$ is H or a linear or branched C$_1$-C$_6$-alkyl group;

R$_3$ is H, R$_2$ or an alcohol protection group.

Step i)

The starting compound, intermediate SM-a, may be obtained from (or easily prepared from compounds obtained from) fermentation products of *Mycobacterium fortuitum* in the presence of an appropriate carbon source.

For example, U.S. Pat. No. 4,029,549 shows the production of 9α-OH BN acid, 9α-OH BN alcohol and 9α-OH BN methyl ester by fermenting the microorganism *Mycobacterium fortuitum* NRRL B-8119 in the presence of either sitosterol (example 2) or cholesterol, stigmasterol or campesterol (example 3). The purification and isolation of 9α-OH BN acid is disclosed in example 5 of U.S. Pat. No. 4,029,549.

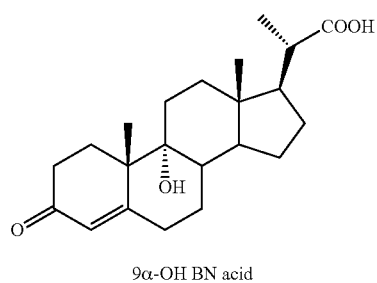

9α-OH BN acid

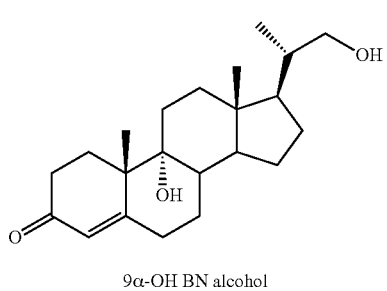

9α-OH BN alcohol

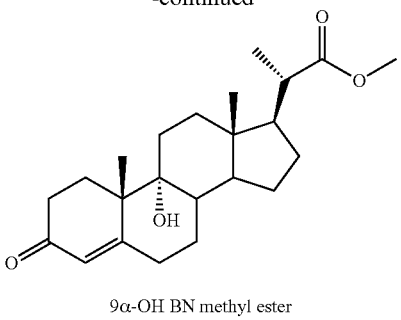

9α-OH BN methyl ester

Accordingly, steps i) to vii) described in the "Synthetic route A" may be preceded by a step comprising cultivating a 9α-OH BN acid-producing microorganism in an aqueous nutrient medium under aerobic conditions in the presence of a carbon source. This applies mutatis mutandis to the other synthetic routes described herein, including "Synthetic route C", "Synthetic route D", "Synthetic route E" and "Synthetic route F".

The 9α-OH BN acid-producing microorganism may be selected from the group consisting of *Arthrobacter, Bacillus, Brevibacterium, Corynebacterium, Microbacterium, Nocardia, Proaminobacter, Serratia, Streptomyces* and *Mycobacterium*. In a preferred embodiment of the invention the 9α-OH BN acid-producing microorganism is *Mycobacterium*, in particular *Mycobacterium fortuitum*. In the most preferred embodiment of the invention the 9α-OH BN acid-producing microorganism is *Mycobacterium fortuitum* NRRL B-8119.

The carbon source may be a steroid, such as cholesterol, stigmasterol, campesterol and sitosterol, preferably sitosterol.

As will be understood, 9α-OH BN acid, 9α-OH BN alcohol and 9α-OH BN methyl ester may, if needed, easily be converted into compounds of the general formula SM-a by standard methods well known to the person skilled in organic chemistry.

Step ii)

Step ii) involves reducing the compound of the general formula SM-a to obtain an intermediate of the general formula Int A1.

The reaction is typically carried out by hydrogenation of SM-a in the presence of palladium on charcoal (Pd/C) at a temperature of 50-90° C., preferably around 70° C., for 1-24 hours, preferably 8-16 hours. Other transition metal catalysts may also be employed, such as Ni or Rh.

If R$_3$ is H, the reaction is preferably carried out in a polar aprotic solvent, such as N-methylpyrrolidone, tetrahydrofuran (THF), ethylacetate (EtOAc), acetone, dimethylformamide (DMF), acetonitrile or dimethyl sulfoxide (DMSO). In a preferred embodiment the polar aprotic solvent is DMF.

If R$_3$ is a C$_1$-C$_6$-alkyl group the reaction is carried out in the corresponding alcohol, i.e. the solvent is an C$_1$-C$_6$-alkanol. In a preferred embodiment of the invention R$_3$ is methyl and the solvent is methanol.

Step iii)

Step iii) involves converting the intermediate of the general formula Int A1 to obtain an intermediate of the general formula Int A2.

The skilled person will be aware of suitable oxidising agents, and examples include chromium oxide (CrO$_3$) and strong acids, such as HI, HBr, HClO$_4$, HCl, HClO$_3$, H$_2$SO$_4$, HNO$_3$, preferably HCl or H$_2$SO$_4$, in particular H$_2$SO$_4$. The reaction is typically carried out in a non-polar solvent, such as dichloromethane (DCM), at a temperature between 0 and 90° C.

Step iv)

Step iv) involves reducing the intermediate of the general formula Int A2 to obtain an intermediate of the general formula Int A3.

The skilled person will be aware of suitable reducing agents capable of reducing a ketone to a secondary alcohol. Preferably, the reducing agent is a metal hydride, such as LiAlH$_4$, NaBH$_4$, LiBH$_4$ or LiAlH(OtBu)$_3$, in particular LiAlH(OtBu)$_3$.

The reaction is typically carried out in a polar aprotic solvent, such as N-methylpyrrolidone, tetrahydrofuran (THF), ethylacetate (EtOAc), acetone, dimethylformamide (DMF), acetonitrile or dimethyl sulfoxide (DMSO), in particular THF, at a temperature between 0 to 20° C.

Step v)

Step v) involves oxidising the intermediate of the general formula Int A3 to obtain an intermediate of the general formula Int A5.

The skilled person will be aware of suitable oxidising agents for performing an allylic oxidation, and a preferred example include chromium oxide (CrO$_3$). Other suitable oxidising agents include tert-butyl hydroperoxide (t-BuO$_2$H), NaOCl, SeO$_2$, pyridinium chlorochromate (PCC), BiCl$_3$ and V$_2$O$_5$. The reaction is typically carried out in a polar solvent, such as AcOH, at a temperature between 0 and 90° C.

Step vi)

Step ii) involves reducing the intermediate of the general formula Int A5 to obtain an intermediate of the general formula Int A6.

The reaction is typically carried out by hydrogenation of Int A5 in the presence of palladium on charcoal (Pd/C) at a temperature of 50-90° C., preferably around 70° C., for 1-24 hours, preferably 8-16 hours. Other transition metal catalysts may also be employed, such as Ni or Rh.

The reaction is preferably carried out in a polar aprotic solvent, such as N-methylpyrrolidone, tetrahydrofuran (THF), ethylacetate (EtOAc), acetone, dimethylformamide (DMF), acetonitrile or dimethyl sulfoxide (DMSO). In a preferred embodiment the polar aprotic solvent is EtOAc.

Step viii)

Step viii) involves reducing the intermediate of the general formula Int A7 to obtain an intermediate of the general formula Int A8.

The skilled person will be aware of suitable reducing agents capable of reducing a carboxylic acid or an ester thereof to a primary alcohol. Preferably, the reducing agent is a metal hydride, such as LiAlH$_4$, NaBH$_4$, LiBH$_4$ or LiAlH(OtBu)$_3$, in particular LiAlH$_4$.

The reaction is typically carried out in a polar aprotic solvent, such as N-methylpyrrolidone, tetrahydrofuran (THF), ethylacetate (EtOAc), acetone, dimethylformamide (DMF), acetonitrile or dimethyl sulfoxide (DMSO), in particular THF, at a temperature between 0 to 50° C.

It should be noted that it is possible to elongate the carbon chain of the intermediate of the general formula Int A7 directly to obtain an intermediate of the general formula Int B2 in a similar way as described in step ix) infra. This may be done by a "Reformatsky reaction", i.e. by reacting Int A7 with Br—CH$_2$—COOR$_2$ in the presence of Zn in a suitable solvent.

Step ix)

Step ix) involves elongating the carbon chain of the compound of the general formula Int A8 to obtain DCA.

Different synthetic routes are possible for elongating the carbon chain of Int A8 to obtain DCA:

One possible route for elongating the carbon chain of Int A8 to obtain DCA comprises the steps ix-a) and ix-b):

ix-a) halogenating the compound of the general formula Int A8 to obtain an intermediate of the general formula Int A9:

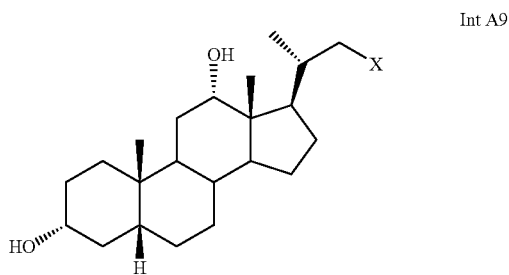

where X is halogen, preferably, Cl, Br or I, in particular Br, optionally acylating Int A9 with a dicarboxylic acid or an dicarboxylic acid derivative to obtain Int A9a.

where R$_3$ is (CH$_2$)$_n$COOH with n being an integer from 0 to 11 included. Acylation of the alcohol in Int A9 can be achieved in a number of ways. For example Int A9 may be reacted with an acyl halide, an anhydride, an ester or condensed with a free carboxylic acid. Alternative Int A9 may be coupled with the carboxylic acid using as suitable coupling reagent known in the art such as DCC, DIC, EDAC.HCl, HATU, TBTU, BOP, PyBOP. The coupling may be performed in the presence of base.

ix-b) elongating the carbon chain of the compound of the general formula Int A9 to obtain DCA:

DCA

Halogenation of primary alcohols is well known to the person skilled in organic chemistry, and may be achieved in various ways. For example, the compound of the general formula Int A8 may be treated with HX, where X is Cl, Br or I, preferably HBr. Alternatively, the compound of the general formula Int A8 may be treated with CX$_4$ and triphenylphosphine (PPh$_3$), where X is Cl, Br or I, preferably Br. In a preferred embodiment of the invention Int A9 is obtained by treating Int A8 with CBr$_4$ and PPh$_3$.

Elongation of the carbon chain of Int A9 to obtain DCA may be carried out using the so-called "Malonic ester synthesis" (see Morrison and Boyd, *Organic Chemistry*, 5$^{th}$ edition, 1987, pp. 1060-1063). In an embodiment of the invention Int A9 is treated with a malonate ester, preferably diethyl malonate, in the presence of a base, preferably NaH, and subsequently acidified to obtain DCA.

Another possible route for elongating the carbon chain of Int A8 to obtain DCA comprises the steps ix-c) to ix-e):
ix-c) oxidising the compound of the general formula Int A8 to obtain an intermediate of the general formula Int B1:

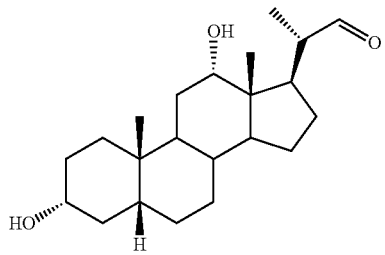

Int B1 ix-d) elongating the carbon chain of the compound of the general formula Int B1 to obtain an intermediate of the general formula Int B2:

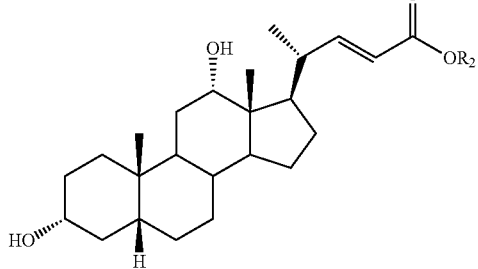

Int B2 where $R_2$ is a linear or branched $C_1$-$C_6$-alkyl group,
ix-e) converting the compound of the general formula Int B2 into DCA.

With respect to step ix-c), oxidation of primary alcohols into aldehydes is well known to the person skilled in organic chemistry, and may be achieved in various ways. For example by chromium-based reagents, such as Collins reagent, PDC or PCC, or by catalytic TEMPO in presence of NaOCl.

Elongation of the carbon chain of Int B1 to Int B2 (step ix-d)) may be carried out using the so-called "Wittig reaction" (see Morrison and Boyd, *Organic Chemistry*, 5$^{th}$ edition, 1987, pp. 920-921). Alternatively, the carbon elongation step may be performed by "Horner-Emmons olefination", by "Peterson olefination", or by a "Reformatsky reaction", i.e. by reacting Int B1 with Br—$CH_2$—$COOR_2$ in the presence of Zn in a suitable solvent.

Conversion of Int B2 to DCA (step ix-e)) may be performed by hydrogenation of Int B2 followed by alkaline hydrolysis, or vice versa.

Step x)

The optional step x) involves converting DCA into a pharmaceutically acceptable salt of DCA.

Examples of pharmaceutically acceptable salts include salts with a base, e.g. salts with an inorganic base, such as a sodium salt, a potassium salt, a calcium salt, a magnesium salt and the like, or salts with an organic base, such as a piperidine salt, a morpholine salt, a pyrrolidoine salt, an arginine salt, a lysine salt and the like. In a preferred embodiment of the invention, the pharmaceutically acceptable salt is the sodium salt.

In a preferred embodiment of the invention the sodium salt of DCA is obtained by reacting DCA with NaOH.

Synthetic Route A'

In another preferred embodiment of the invention, the process for the preparation of deoxycholic acid (DCA) or a pharmaceutically acceptable salt thereof, comprises the following steps:

i) providing a compound of the general formula

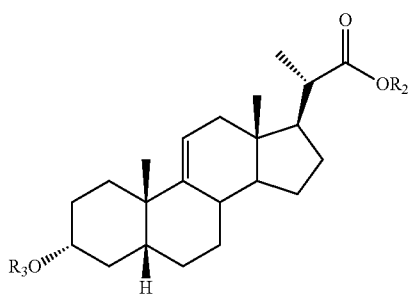

Int A3 ii) oxidising the intermediate of the general formula Int A3 into an intermediate of the general formula Int A5:

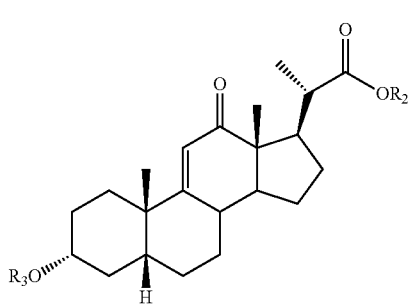

Int A5 iii) reducing the intermediate of the general formula Int A5 into an intermediate of the general formula Int A6:

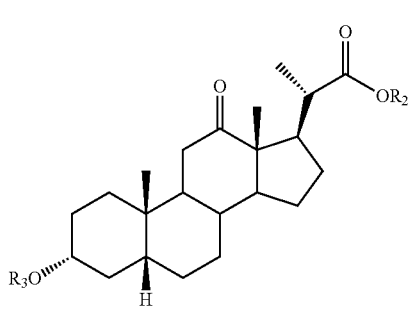

Int A6 iv) reducing the intermediate of the general formula Int A6 into an intermediate of the general formula Int A7:

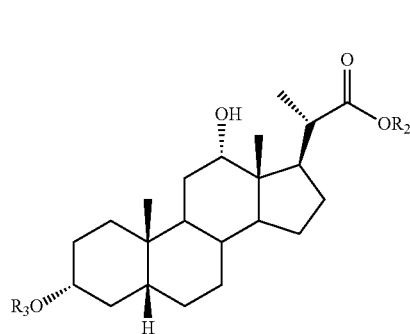

v) reducing the compound of the general formula Int A7 into an intermediate of the general formula Int A8:

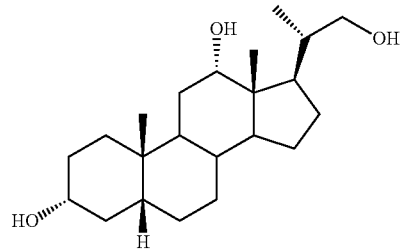

vi) elongating the carbon chain of the compound of the general formula Int A8 to obtain deoxycholic acid (DCA):

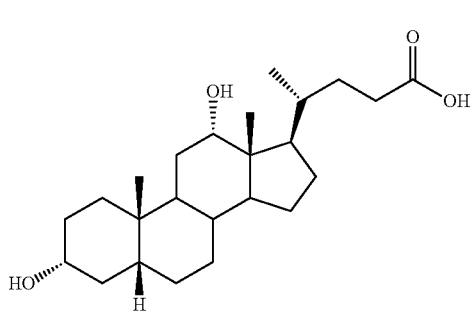

vii) optionally converting deoxycholic acid to a pharmaceutically acceptable salt thereof,
wherein
R₂ is H or a linear or branched $C_1$-$C_6$-alkyl group;
R₃ is H, R₂ or an alcohol protection group.

Steps ii) to vii) above corresponds exactly to steps v) to x) discussed in connection with "Synthetic Route A". The comments provided for steps v) to x) in connection with "Synthetic Route A" therefore apply mutatis mutandis to steps ii) to vii) of the "Synthetic Route A'".

Synthetic Route C

In another interesting embodiment of the invention, the process for the preparation of deoxycholic acid (DCA) or a pharmaceutically acceptable salt thereof, comprises the following steps:

i) providing a compound of the general formula SM-a:

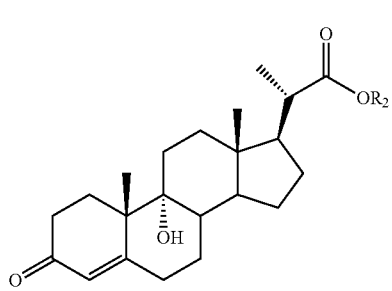

ii) reducing the compound of the general formula SM-a to obtain an intermediate of the general formula Int A1:

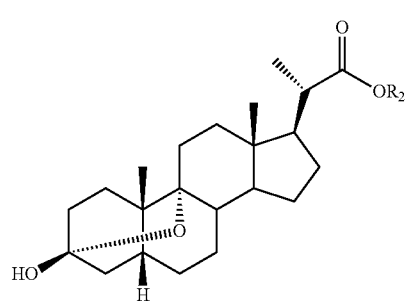

iii) converting the intermediate of the general formula Int A1 into an intermediate of the general formula Int A2:

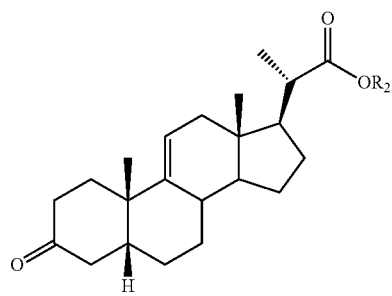

iv) oxidising the intermediate of the general formula Int 2A into an intermediate of the general formula Int C1:

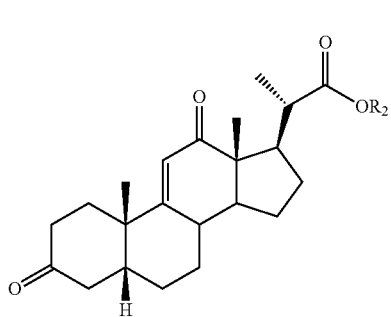

v) reducing the intermediate of the general formula Int C1 into an intermediate of the general formula Int C4:

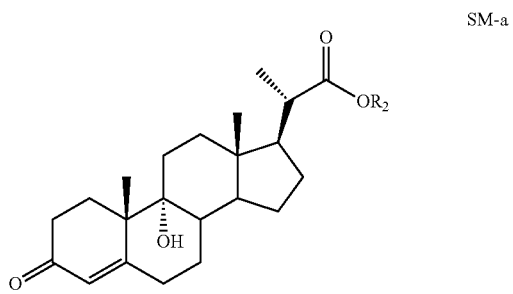

vi) reducing the compound of the general formula Int C4 into an intermediate of the general formula Int A8:

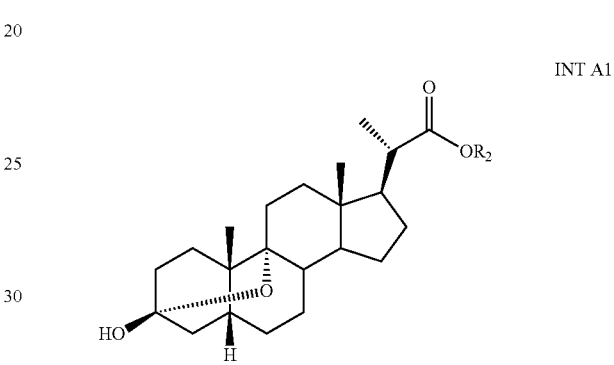

vii) elongating the carbon chain of the compound of the general formula Int A8 to obtain deoxycholic acid (DCA):

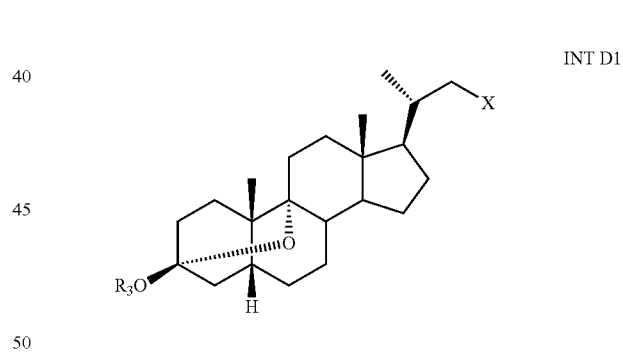

viii) optionally converting deoxycholic acid to a pharmaceutically acceptable salt thereof, wherein $R_2$ is H or a linear or branched $C_1$-$C_6$-alkyl group;

$R_3$ is H, $R_2$ or an alcohol protection group.

x) optionally converting deoxycholic acid to a pharmaceutically acceptable salt thereof, wherein $R_2$ is H or a linear or branched $C_1$-$C_6$-alkyl group.

Synthetic Route D

In still another interesting embodiment of the invention, the process for the preparation of deoxycholic acid (DCA) or a pharmaceutically acceptable salt thereof, comprises the following steps:

i) providing a compound of the general formula SM-a:

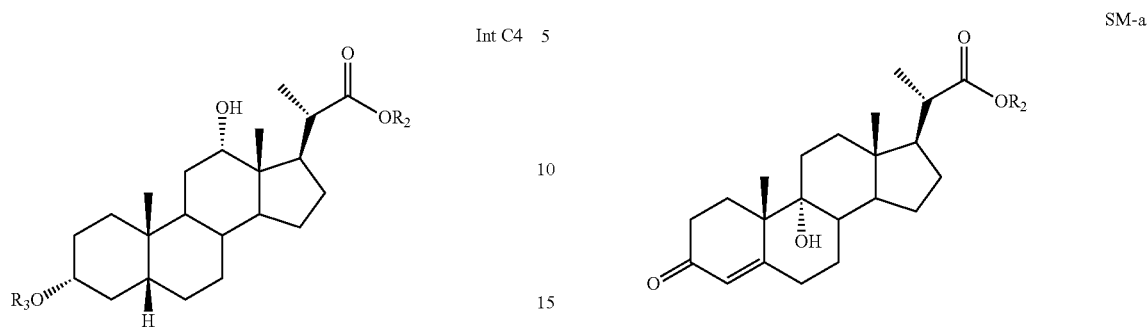

ii) reducing the compound of the general formula SM-a to obtain an intermediate of the general formula Int A1:

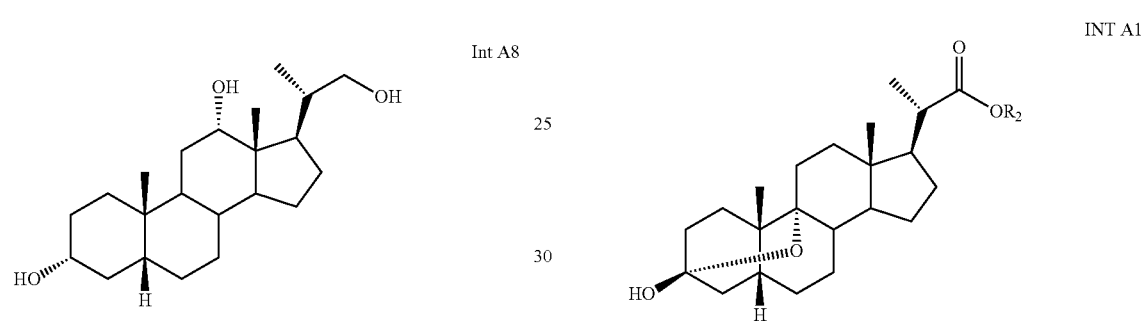

iii) converting the intermediate of the general formula A1 into an intermediate of the general formula D1:

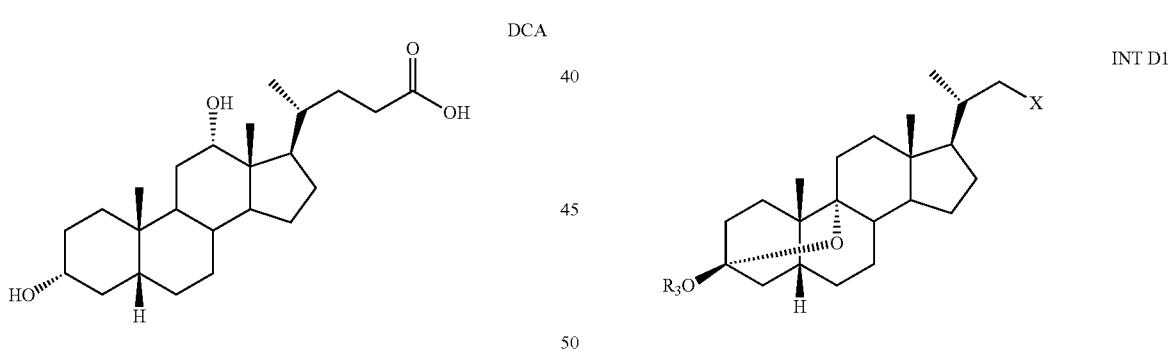

iv) oxidising the intermediate of the general formula Int D1 into an intermediate of the general formula Int D2:

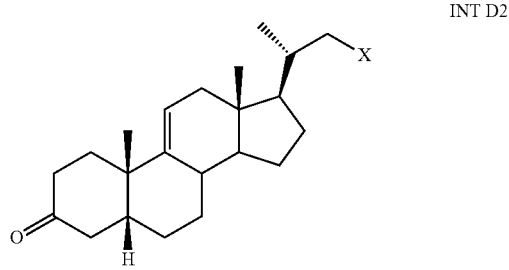

v) reducing the intermediate of the general formula Int D2 into an intermediate of the general formula Int D3:

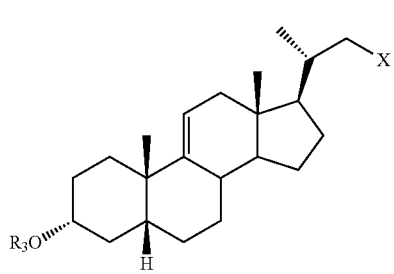
Int D3 vi) oxidising the intermediate of the general formula Int D3 into an intermediate of the general formula Int D5:

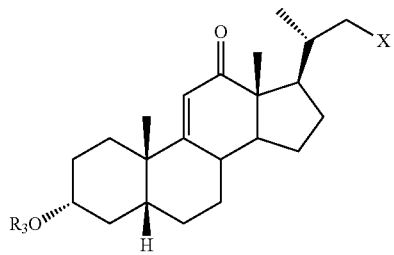
Int D5 vii) reducing the intermediate of the general formula Int D5 into an intermediate of the general formula Int D6:

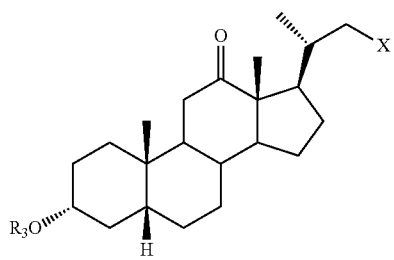
Int D6 viii) reducing the intermediate of the general formula Int D6 into an intermediate of the general formula Int D7:

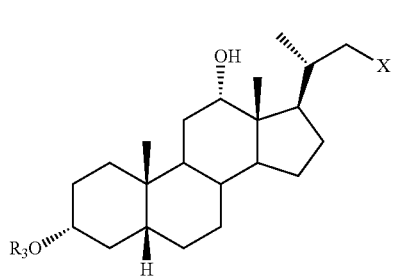
Int D7 ix) hydrolysing the compound of the general formula Int D7 into an intermediate of the general formula Int D9:

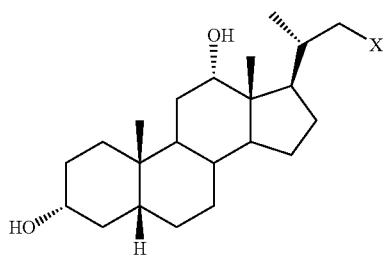
Int D9 x) elongating the carbon chain of the compound of the general formula Int D9 to obtain an deoxycholic acid (DCA):

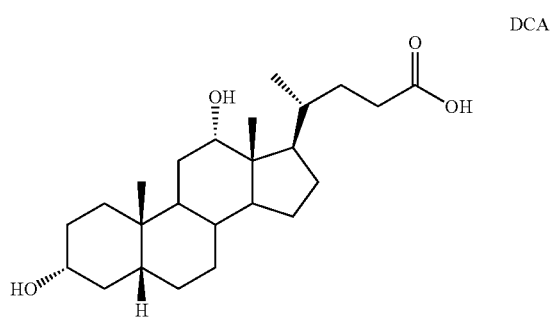
DCA xi) optionally converting deoxycholic acid to a pharmaceutically acceptable salt thereof, wherein $R_2$ is H or a linear or branched $C_1$-$C_6$-alkyl group;

$R_3$ is H, $R_2$ or an alcohol protection group;

and X is a halogen atom.

Synthetic Route D'

In another interesting embodiment of the invention, the process for the preparation of deoxycholic acid (DCA) or a pharmaceutically acceptable salt thereof, comprises the following steps:

i) providing a compound of the general formula Int D3:

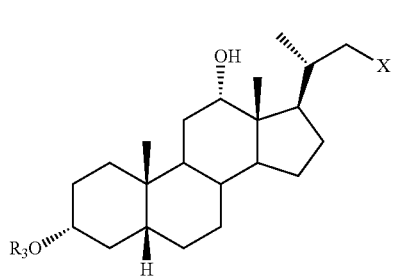
Int D3 ii) oxidising the intermediate of the general formula Int D3 into an intermediate of the general formula Int D5:

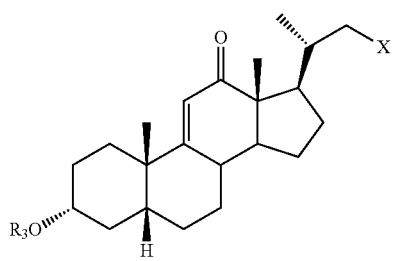
Int D5 iii) reducing the intermediate of the general formula Int D5 into an intermediate of the general formula Int D6:

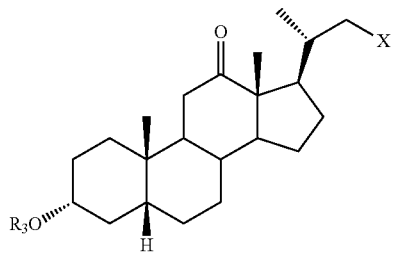
Int D6 iv) reducing the intermediate of the general formula Int D6 into an intermediate of the general formula Int D7:

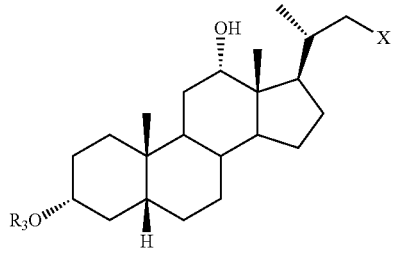
Int D7 v) hydrolysing the compound of the general formula Int D7 into an intermediate of the general formula Int D9:

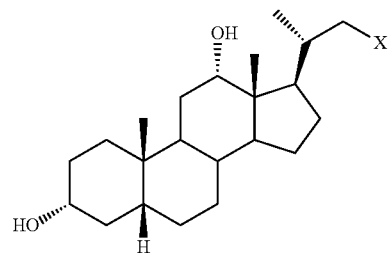
Int D9 vi) elongating the carbon chain of the compound of the general formula Int D9 to obtain an deoxycholic acid (DCA):

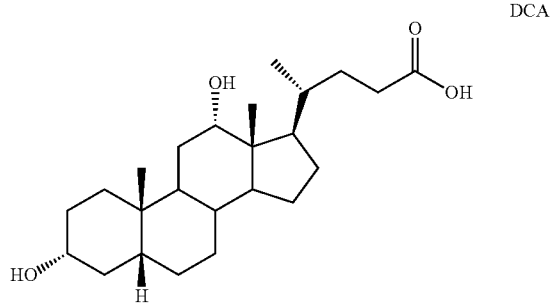
DCA vii) optionally converting deoxycholic acid to a pharmaceutically acceptable salt thereof, wherein $R_2$ is H or a linear or branched $C_1$-$C_6$-alkyl group;

$R_3$ is H, $R_2$ or an alcohol protection group;

and X is a halogen atom.

Synthetic Route E

In yet another interesting embodiment of the invention, the process for the preparation of deoxycholic acid (DCA) or a pharmaceutically acceptable salt thereof, comprises the following steps:

i) providing a compound of the general formula SM-a:

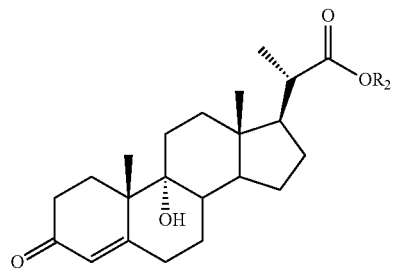
SM-a ii) reducing the compound of the general formula SM-a to obtain an intermediate of the general formula SM-b:

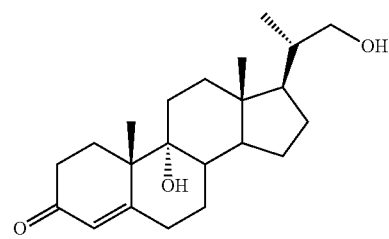
SM-b iii) protecting the alcohol group at position 22 to obtain an intermediate of the general formula Int E1:

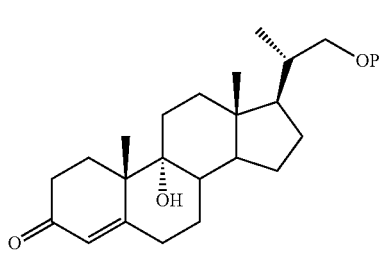

Int E1 iv) converting the compound of the general formula Int E1 to obtain an intermediate of the general formula Int E2:

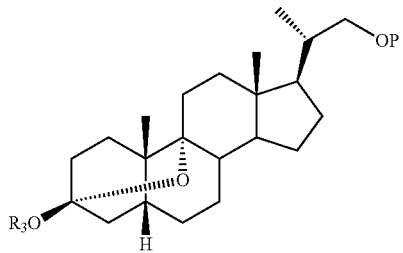

Int E2 v) dehydration of the intermediate of the general formula Int E2 into an intermediate of the general formula Int E3:

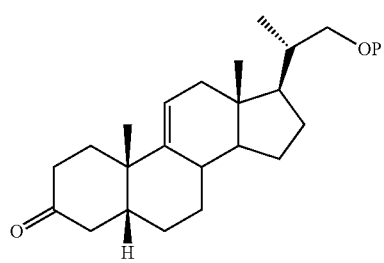

Int E3 vi) reducing the intermediate of the general formula Int E3 into an intermediate of the general formula Int E5:

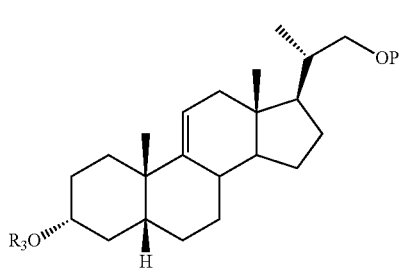

Int E5 vii) oxidising the intermediate of the general formula Int E5 into an intermediate of the general formula Int E6:

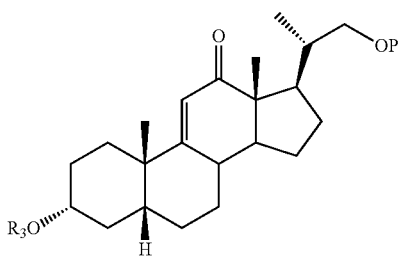

Int E6 viii) reducing the intermediate of the general formula Int E6 into an intermediate of the general formula Int E7:

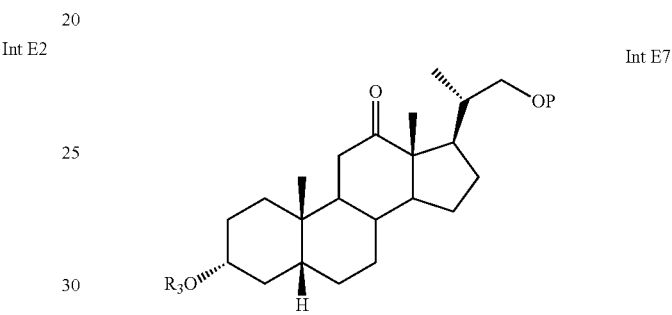

Int E7 ix) reducing the intermediate of the general formula Int E7 into an intermediate of the general formula Int E9

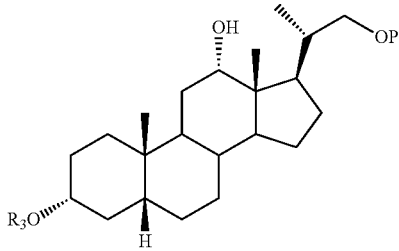

Int E9 x) elongating the carbon chain of the compound of the general formula Int E9 to obtain an deoxycholic acid (DCA):

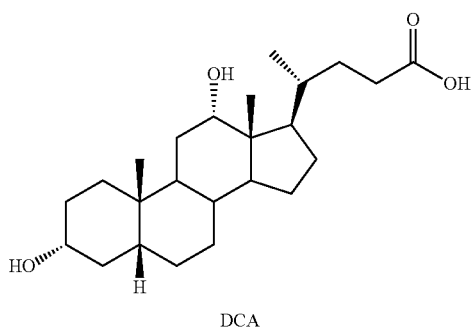

DCA x) optionally converting deoxycholic acid to a pharmaceutically acceptable salt thereof, wherein $R_2$ is H or a linear or branched $C_1$-$C_6$-alkyl group;

$R_3$ is H, $R_2$ or an alcohol protection group; and

P is an alcohol protection group.

Synthetic Route E'

In another interesting embodiment of the invention, the process for the preparation of deoxycholic acid (DCA) or a pharmaceutically acceptable salt thereof, comprises the following steps:

i) providing a compound of the general formula Int E3:

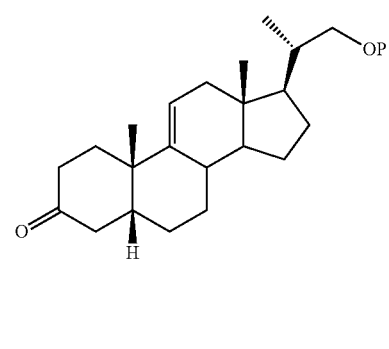

Int E3 ii) reducing the intermediate of the general formula Int E3 into an intermediate of the general formula Int E5:

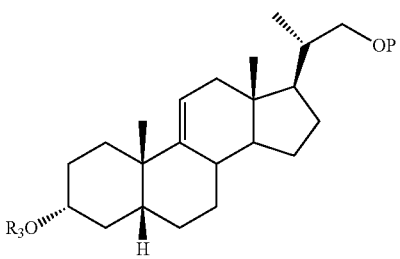

Int E5 iii) oxidising the intermediate of the general formula Int E5 into an intermediate of the general formula Int E6:

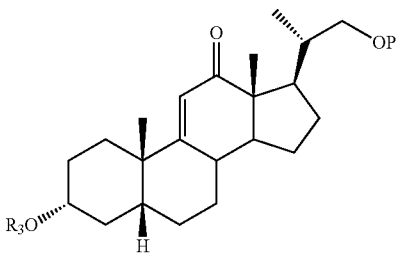

Int E6 iv) reducing the intermediate of the general formula Int E6 into an intermediate of the general formula Int E7:

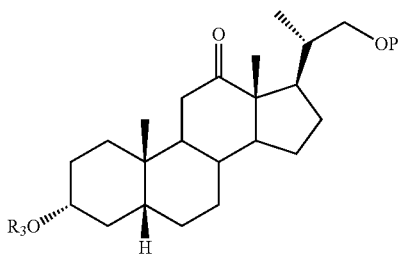

Int E7 v) reducing the intermediate of the general formula Int E7 into an intermediate of the general formula Int E9

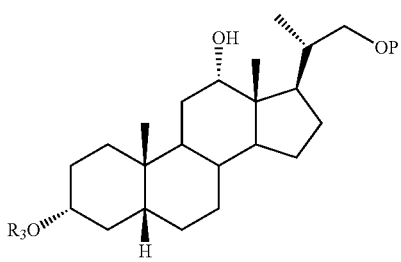

Int E9 vi) elongating the carbon chain of the compound of the general formula Int E9 to obtain an deoxycholic acid (DCA):

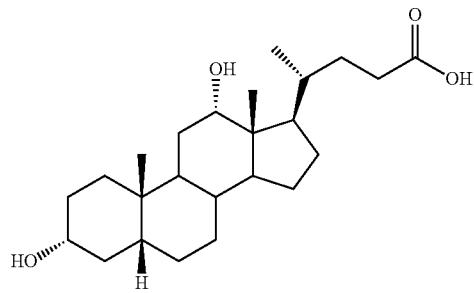

DCA vii) optionally converting deoxycholic acid to a pharmaceutically acceptable salt thereof, wherein $R_2$ is H or a linear or branched $C_1$-$C_6$-alkyl group;

$R_3$ is H, $R_2$ or an alcohol protection group; and

P is an alcohol protection group.

Synthetic Route F

In still another interesting embodiment of the invention, the process for the preparation of deoxycholic acid (DCA) or a pharmaceutically acceptable salt thereof, comprises the following steps:

i) providing a compound of the general formula SM-a:

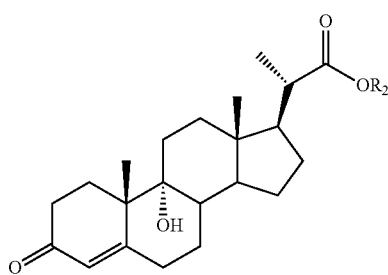

SM-a ii) reducing the compound of the general formula SM-a to obtain an intermediate of the general formula SM-b:

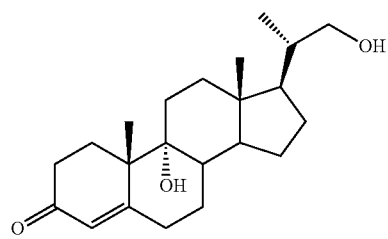

SM-b iii) protecting the alcohol group at position 22 to obtain an intermediate of the general formula Int E1:

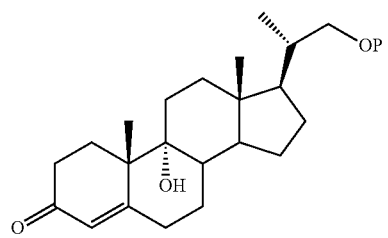

Int E1 iv) converting the compound of the general formula Int E1 into an intermediate of the general formula Int F2:

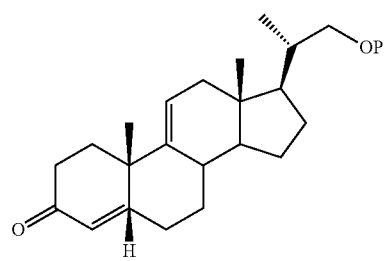

Int F2 v) reducing the intermediate of the general formula Int F2 into an intermediate of the general formula Int E3:

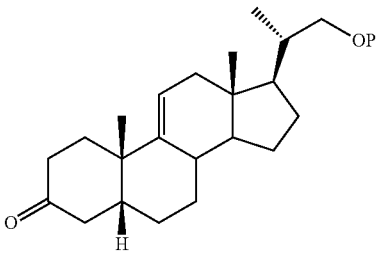

Int E3 vi) reducing the intermediate of the general formula Int E3 into an intermediate of the general formula Int E5:

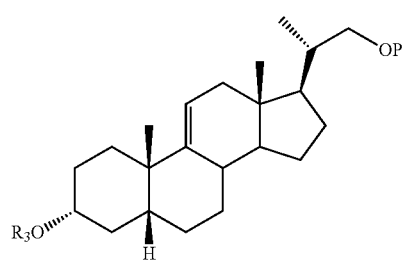

Int E5 vii) oxidising the intermediate of the general formula Int E5 into an intermediate of the general formula Int E6:

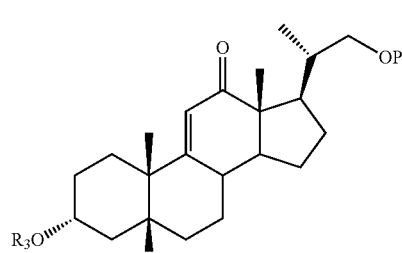

Int E6 viii) reducing the intermediate of the general formula Int E6 into an intermediate of the general formula Int E7:

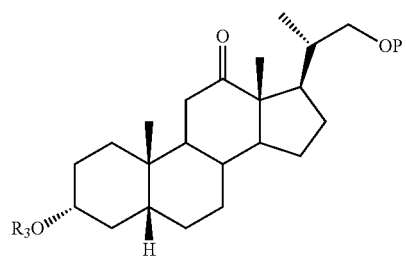

Int E7 ix) reducing the intermediate of the general formula Int E7 into an intermediate of the general formula Int E9

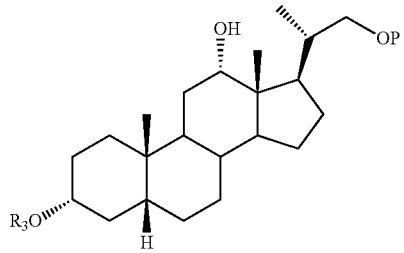

Int E9 x) elongating the carbon chain of the compound of the general formula Int E9 to obtain an deoxycholic acid (DCA):

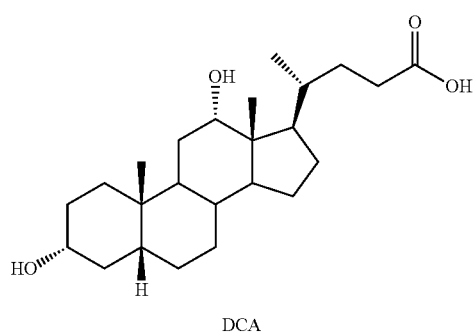

DCA x) optionally converting deoxycholic acid to a pharmaceutically acceptable salt thereof, wherein $R_2$ is H or a linear or branched $C_1$-$C_6$-alkyl group;
$R_3$ is H, $R_2$ or an alcohol protection group; and
P is an alcohol protection group.

The Intermediate Compounds

The Starting Compound—The Intermediate of the General Formula SM

In a further aspect, the present invention relates to a compound of the general formula SM

SM

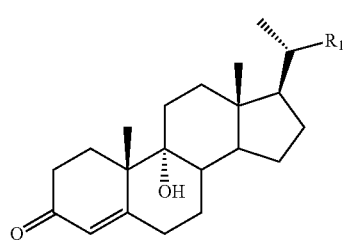

wherein
$R_1$ is $COOR_2$, $CH_2OP$, $CH_2X$, $CH_2CHO$, $CH_2$—$CH_2$—OH, $CH_2$—$CH_2OP$, $CH_2$—$CH_2X$ or $CH_2$—$CH_2$—CHO;
$R_2$ is a linear or branched $C_1$-$C_6$-alkyl group with the proviso that $R_2$ is not $CH_3$;

P is an alcohol protection group with the proviso that P is not Ac; and
X is a halogen atom.

In a preferred embodiment of the invention, $R_1$ is $COOR_2$ or $CH_2X$ where $R_2$ is selected from the group consisting of ethyl, n-propyl and iso-propyl, in particular ethyl, and X is selected from the group consisting of Cl, Br and I, in particular Br.

Accordingly, in one particular interesting embodiment of the invention $R_1$ is $COOC_2H_5$, and in another particular interesting embodiment of the invention $R_2$ is $CH_2Br$.

Such compounds can be obtained from (or easily prepared from compounds obtained from) fermentation products of *Mycobacterium fortuitum* in the presence of an appropriate carbon source.

For example, U.S. Pat. No. 4,029,549 shows the production of 9α-OH BN acid, 9α-OH BN alcohol and 9α-OH BN methyl ester by fermenting the microorganism *Mycobacterium fortuitum* NRRL B-8119 in the presence of either sitosterol (example 2) or cholesterol, stigmasterol or campesterol (example 3). The purification and isolation of 9α-OH BN acid is disclosed in example 5 of U.S. Pat. No. 4,029,549.

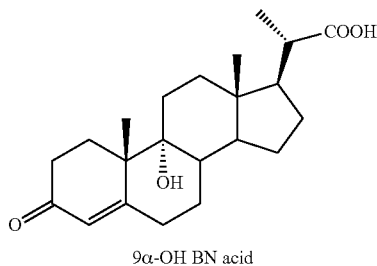

9α-OH BN acid

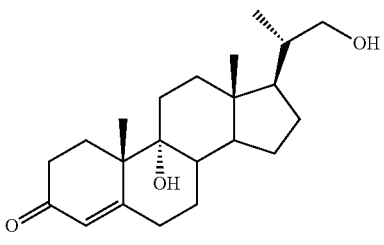

9α-OH BN alcohol

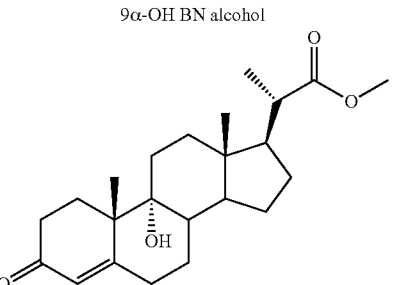

9α-OH BN methyl ester

Accordingly, steps I) to VI) described herein may be preceded by a step comprising cultivating a 9α-OH BN acid-producing microorganism in an aqueous nutrient medium under aerobic conditions in the presence of a carbon source.

The 9α-OH BN acid-producing microorganism may be selected from the group consisting of *Arthrobacter, Bacillus, Brevibacterium, Corynebacterium, Microbacterium, Nocardia, Proaminobacter, Serratia, Streptomyces* and *Mycobac-* terium. In a preferred embodiment of the invention the 9α-OH BN acid-producing microorganism is *Mycobacterium*, in particular *Mycobacterium fortuitum*. In the most preferred embodiment of the invention the 9α-OH BN acid-producing microorganism is *Mycobacterium fortuitum* NRRL B-8119.

The carbon source may be a steroid, such as cholesterol, stigmasterol, campesterol and sitosterol, preferably sitosterol.

As will be understood, 9α-OH BN acid, 9α-OH BN alcohol and 9α-OH BN methyl ester may, if needed, easily be converted into compounds of the general formula SM by standard methods well known to the person skilled in organic chemistry.

The Intermediate of the General Formula INT 1

In a still further aspect, the present invention relates to a compound of the general formula INT 1

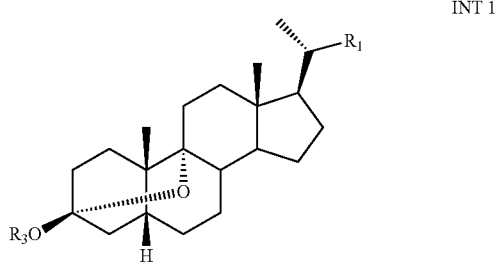

INT 1 wherein
$R_1$ is $COOR_2$, $CH_2OH$, $CH_2OP$, $CH_2X$, $CH_2CHO$, $CH_2$—$CH_2$—$OH$, $CH_2$—$CH_2OP$, or $CH_2$—$CH_2X$ or $CH_2$—$CH_2$—$CHO$;
$R_2$ is H or a linear or branched $C_1$-$C_6$-alkyl group;
P is an alcohol protection group;
$R_3$ either P or $R_2$; and
X is a halogen atom.

In a preferred embodiment of the invention, $R_1$ is $COOR_2$, $CH_2X$, $CH_2OH$ or $CH_2OP$ where $R_2$ is H or selected from the group consisting of methyl, ethyl, n-propyl and iso-propyl, in particular H or methyl, and X is selected from the group consisting of Cl, Br and I, in particular Br.

In a more preferred embodiment of the invention $R_1$ is $COOR_2$, $CH_2X$, $CH_2OH$ or $CH_2OP$ where $R_2$ is H or methyl, and X is Br.

In an even more preferred embodiment of the invention, $R_1$ is $COOR_2$ where $R_2$ is H or selected from the group consisting of methyl, ethyl, n-propyl and iso-propyl, in particular H or methyl, and X is selected from the group consisting of Cl, Br and I, in particular Br.

Accordingly, in one particular interesting embodiment of the invention $R_1$ is COOH or $COOCH_3$ and $R_3$ is H or $CH_3CO$. Specific examples include embodiments where $R_1$ is COOH and $R_3$ is H, where $R_1$ is $COOCH_3$ and $R_3$ is H, where $R_1$ is COOH and $R_3$ is $CH_3CO$, and where $R_1$ is $COOCH_3$ and $R_3$ is $CH_3CO$.

In another highly preferred embodiment of the invention, $R_1$ is $CH_2OH$ and $R_3$ is either H or $CH_3CO$.

In a further highly preferred embodiment of the invention, $R_1$ is $CH_2X$ and $R_3$ is either H or $CH_3CO$, and X is selected from the group consisting of Cl, Br and I, in particular Br. Specific examples include embodiments where $R_1$ is $CH_2Br$ and $R_3$ is H, and where $R_1$ is $CH_2Br$ and $R_3$ is $CH_3CO$.

In a still further highly preferred embodiment of the invention $R_1$ is $CH_2OP$ and $R_3$ is either H or $CH_3CO$, wherein P is selected from the group consisting of trimethylsilyl ether (TMS), triethylsilyl ether (TES), triisopropylsilyl ether (TIPS), tert-butyldimethylsilyl ether (TBS, TBDMS), tert-butyldiphenylsilyl ether (TBDPS), acetyl (Ac, $COCH_3$), benzoyl (Bz), benzyl ether (Bn), 4-methoxybenzyl ether (PMB), 2-naphthylmethyl ether (Nap), methoxymethyl acetal (MOM), 2-methoxyethoxy-methyl ether (MEM), ethoxyethyl acetal (EE), methoxypropyl acetal (MOP), benzyloxymethyl acetal (BOM), tetrahydropyranyl acetal (THP), 2,2,2-trichloro-ethyl carbonate (Troc), methyl ether, dimethoxytrityl (DMT), methoxytrityl (MMT), methylthiomethyl ether, pivaloyl (Piv), tetrahydropyranyl (THP), triphenylmethyl (trityl, Tr), and tosyl (Ts), in particular Ac, TBDMS and Ts.

Thus, specific embodiments include examples where $R_1$ is $CH_2OAc$ and $R_3$ is H, where $R_1$ is $CH_2OAc$ and $R_3$ is $CH_3CO$, where $R_1$ is $CH_2OTBDMS$ and $R_3$ is H, where $R_1$ is $CH_2OTBDMS$ and $R_3$ is $CH_3CO$, where $R_1$ is $CH_2OTs$ and $R_3$ is H, and where $R_1$ is $CH_2OTs$ and $R_3$ is $CH_3CO$.

Compounds of the general formula INT 1 may easily be prepared by reducing compounds of the general formula SM by methods well known to the person skilled in organic chemistry, as described herein.

The Intermediate of the General Formula INT 2

In a still further aspect, the present invention relates to a compound of the general formula INT 2

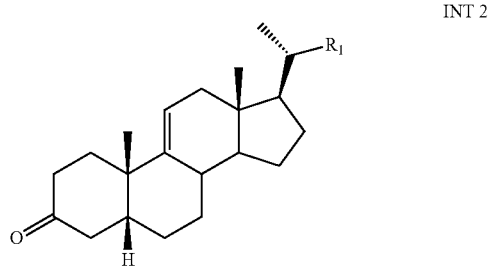

INT 2 wherein
$R_1$ is $COOR_2$, $CH_2OH$, $CH_2OP$, $CH_2X$, $CH_2CHO$, $CH_2$—$CH_2$—$OH$, $CH_2$—$CH_2OP$, $CH_2$—$CH_2X$ or $CH_2$—$CH_2$—$CHO$;
$R_2$ is H or a linear or branched $C_1$-$C_6$-alkyl group;
P is an alcohol protection group; and
X is a halogen atom.

In a preferred embodiment of the invention, $R_1$ is $COOR_2$, $CH_2X$, $CH_2OH$ or $CH_2OP$ where $R_2$ is H or selected from the group consisting of methyl, ethyl, n-propyl and iso-propyl, in particular methyl, and X is selected from the group consisting of Cl, Br and I, in particular Br.

In a more preferred embodiment of the invention $R_1$ is $COOR_2$, $CH_2X$, $CH_2OH$ or $CH_2OP$ where $R_2$ is methyl, and X is Br.

Accordingly, in one particular interesting embodiment of the invention $R_1$ is $COOCH_3$. In another particular interesting embodiment of the invention $R_1$ is $CH_2Br$. In a further particular interesting embodiment of the invention $R_1$ is $CH_2OH$.

In a further highly preferred embodiment of the invention $R_1$ is $CH_2OP$, wherein P is selected from the group consisting of trimethylsilyl ether (TMS), triethylsilyl ether (TES), triisopropylsilyl ether (TIPS), tert-butyldimethylsilyl ether (TBS, TBDMS), tert-butyldiphenylsilyl ether (TBDPS), acetyl (Ac, COCH$_3$), benzoyl (Bz), benzyl ether (Bn), 4-methoxybenzyl ether (PMB), 2-naphthylmethyl ether (Nap), methoxymethyl acetal (MOM), 2-methoxyethoxy-methyl ether (MEM), ethoxyethyl acetal (EE), methoxypropyl acetal (MOP), benzyloxymethyl acetal (BOM), tetrahydropyranyl acetal (THP), 2,2,2-trichloro-ethyl carbonate (Troc), methyl ether, dimethoxytrityl (DMT), methoxytrityl (MMT), methylthiomethyl ether, pivaloyl (Piv), tetrahydropyranyl (THP), triphenylmethyl (trityl, Tr), and tosyl (Ts), in particular Ac, TBDMS and Ts. Thus, specific embodiments include examples where R$_1$ is CH$_2$OAc, where R$_1$ is CH$_2$OTBDMS and where R$_1$ is CH$_2$OTs.

Compounds of the general formula INT 2 may easily be prepared by oxidising compounds of the general formula INT 1 by methods well known to the person skilled in organic chemistry, as described herein.

The Intermediate of the General Formula INT 3

In an even further aspect, the present invention relates to a compound of the general formula INT 3

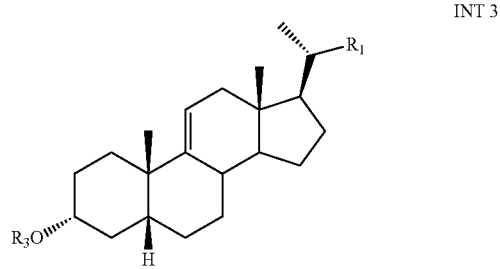

INT 3 wherein
R$_1$ is COOR$_2$, CH$_2$OH, CH$_2$OP, CH$_2$X, CH$_2$CHO, CH$_2$—CH$_2$—OH, CH$_2$—CH$_2$OP, CH$_2$—CH$_2$X or CH$_2$—CH$_2$—CHO;
R$_2$ is H or a linear or branched C$_1$-C$_6$-alkyl group; P is an alcohol protection group;
R$_3$ is either P or R$_2$; and
X is a halogen atom;
with the proviso that R$_1$ is not CH$_2$—CH$_2$—OH when R$_3$ is H; R$_1$ is not CH$_2$—CH$_2$OAc when R$_3$ is Ac; and R$_1$ is not COOCH$_3$ when R$_3$ is Ac.

In a preferred embodiment of the invention, R$_1$ is COOR$_2$, CH$_2$X, CH$_2$OH or CH$_2$OP where R$_2$ is selected from the group consisting of ethyl, n-propyl and iso-propyl, in particular ethyl, and X is selected from the group consisting of Cl, Br and I, in particular Br.

In an interesting embodiment of the invention R$_1$ is COOCH$_3$ and R$_3$ is H.

In another interesting embodiment of the invention R$_1$ is CH$_2$X, wherein X is selected from the group consisting of Cl, Br and I, and R$_3$ is H or Ac. Particular examples are where X is Br and R$_3$ is H, and where X is Br and R$_3$ is Ac.

In another interesting embodiment of the invention R$_1$ is CH$_2$OP and R$_3$ is either H or CH$_3$CO, wherein P is selected from the group consisting of trimethylsilyl ether (TMS), triethylsilyl ether (TES), triisopropylsilyl ether (TIPS), tert-butyldimethylsilyl ether (TBS, TBDMS), tert-butyldiphenylsilyl ether (TBDPS), acetyl (Ac, COCH$_3$), benzoyl (Bz), benzyl ether (Bn), 4-methoxybenzyl ether (PMB), 2-naphthylmethyl ether (Nap), methoxymethyl acetal (MOM), 2-methoxyethoxy-methyl ether (MEM), ethoxyethyl acetal (EE), methoxypropyl acetal (MOP), benzyloxymethyl acetal (BOM), tetrahydropyranyl acetal (THP), 2,2,2-trichloro-ethyl carbonate (Troc), methyl ether, dimethoxytrityl (DMT), methoxytrityl (MMT), methylthiomethyl ether, pivaloyl (Piv), tetrahydropyranyl (THP), triphenylmethyl (trityl, Tr), and tosyl (Ts), in particular Ac, TBDMS and Ts. Thus, specific embodiments include examples where R$_1$ is CH$_2$OAc and R$_3$ is H, where R$_1$ is CH$_2$OAc and R$_3$ is CH$_3$CO, where R$_1$ is CH$_2$OTBDMS and R$_3$ is H, where R$_1$ is CH$_2$OTBDMS and R$_3$ is CH$_3$CO, where R$_1$ is CH$_2$OTs and R$_3$ is H, and where R$_1$ is CH$_2$OTs and R$_3$ is CH$_3$CO.

Compounds of the general formula INT 3 may easily be prepared by reducing compounds of the general formula INT 2 by methods well known to the person skilled in organic chemistry, as described herein.

As will be understood, the intermediates disclosed herein can be used for the preparation of DCA and pharmaceutically acceptable salts thereof. Since the synthetic routes described herein allow for introduction of an —OH group in position 12, it is contemplated that the same intermediates will also be suitable for preparing other bile acids, which include an —OH group in position 7. Specific examples of such bile salts include cholic acid, glycocholic acid, taurocholic acid, or a pharmaceutically acceptable salt thereof.

EXAMPLES

Example 1

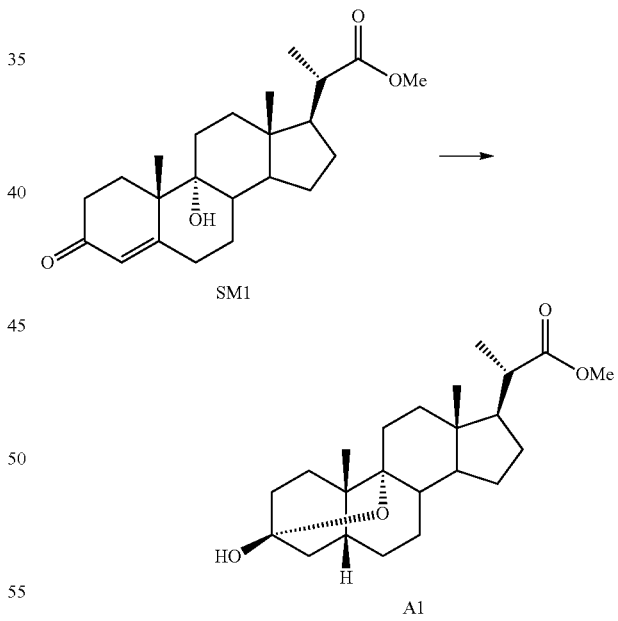

40 g of compound SM1 (106.80 mmol) was suspended in 150 ml of DMF, then 2.77 g of dry Pd/C 10% was added. The reaction mixture was stirred at 70° C. and hydrogenated (3.5 atm) overnight. The mixture was filtered through Celite®. Then, the mixture was poured over water forming a precipitate. The precipitate was filtered off as a white solid, washed with water and dried under vacuum, thereby yielding 39.3 g of compound A1.

$^1$H NMR (400 MHz, CDCl$_3$): δ 3.56 (s, 3H); 2.30 (m, 1H); 1.10 (d, 3H); 0.87 (s, 3H); 0.62 (s, 3H).

Example 2

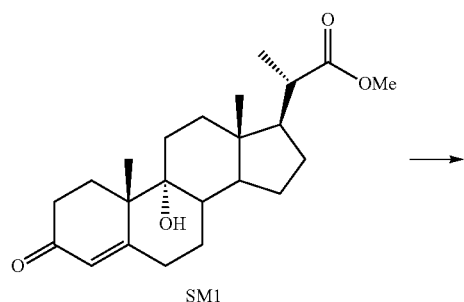
SM1

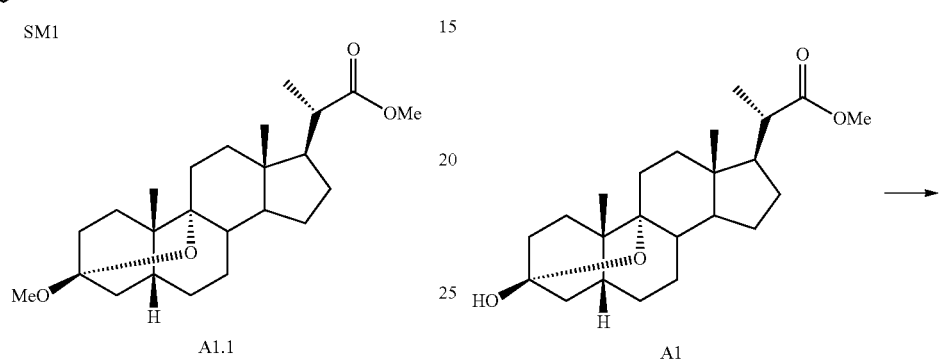

20 g of compound SM1 (53.40 mmol) was suspended in 150 ml of MeOH, then 1.4 g of dry Pd/C 10% was added. The reaction mixture was stirred at 70° C. and hydrogenated (1.0 atm) overnight. 1.0 g of p-TsOH (10% molar, 5.3 mmol) was added and stirred for 8 h. The mixture was filtered through Celite®. The solvent was evaporated under vacuum. The solid was recrystallized in 60 ml of EtOH. The solid was filtered off and dried under vacuum, yielding 18.8 g of compound A1.1.

Example 3

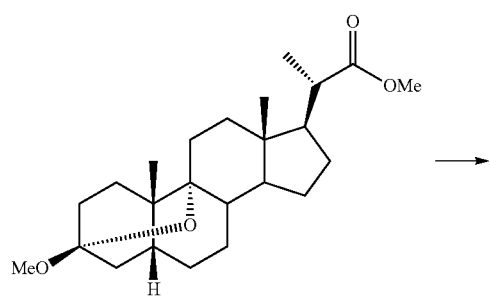
A1.1

LiAlH$_4$ (1.88 g, 49.63 mmol, 1.3 eq.) and THF (20 ml) were mixed in an inert atmosphere. A mixture of A1.1 (14.0 g) and 40 ml of THF was added dropwise. The mixture was stirred overnight at room temperature until the reaction was completed. The mixture was then cooled at 0-5° C. and was quenched by dropwise addition of an aqueous solution of Na$_2$SO$_4$.10H$_2$O (16.20 g) and THF (50 ml). The precipitate was filtered off, the solvent was evaporated under reduced pressure. The solid was recrystallized in 150 ml EtOH. The solid was filtered off and dried under vacuum, thereby yielding 10.15 g of D1.

Example 4

39, 3 g of A1 (104.37 mmol) was dissolved in DCM (100 ml) and stirred at room temperature. Sulphuric acid (9.29 g, 0.9 eqv) was added at 10° C., then the mixture is stirred overnight. The reaction mixture was worked up by washing with water and NaHCO$_3$ and he organic layer was separated. The organic layer was concentrated followed by column chromatography to yield 28.8 g of A2.

$^1$H NMR (400 MHz, CDCl$_3$): δ 5.50 (s, 1H); 3.57 (s, 3H); 1.15 (d, 3H); 1.09 (s, 3H); 0.59 (s, 3H).

Example 5

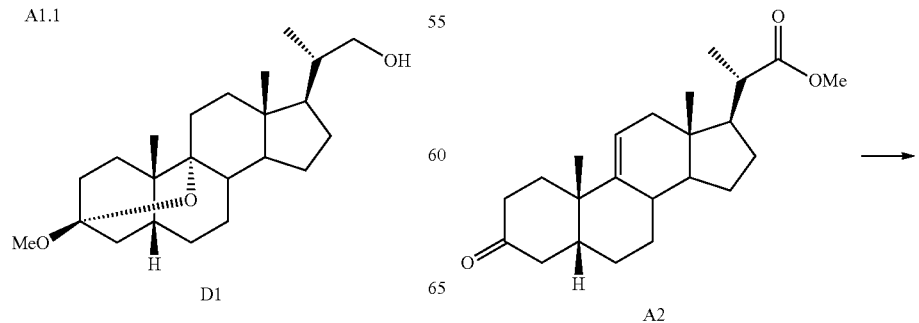

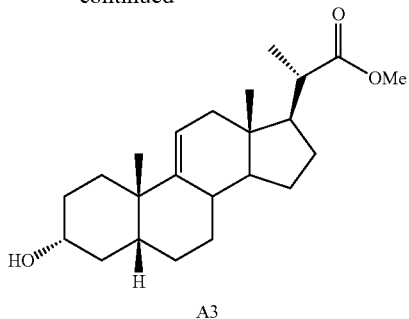

A3

28.6 g of A2 (79.87 mmol) was dissolved and stirred in THF (100 ml) under inert atmosphere. The solution was cooled at 0-5° C. and LiAlH(OtBu)$_3$ (22.34 g, 1.1 eqv) was added slowly (exothermic reaction). The mixture was stirred at room temperature until the reaction was complete. The mixture was cooled at 0-5° C. and was hydrolyzed slowly with a solution of 1M HCl. The aqueous phase was extracted with EtOAc and the organic phase is washed with a solution of NaHCO$_3$. The solvent was evaporated under reduced pressure, yielding 27.62 g of A3. $^1$H NMR (400 MHz, CDCl$_3$): δ 0.59 (s, 3H); 1.05 (s, 3H); 1.18 (d, 3H); 2.43 (m, 2H); 3.65 (s, 3H); 3.65 (m, 1H); 5.32 (dd, 1H).

$^1$H NMR (400 MHz, CDCl$_3$): δ 5.29 (s, 1H); 3.57 (s, 3H); 3.39 (m, 1H); 1.11 (d, 3H); 1.01 (s, 3H); 0.55 (s, 3H).

Example 6

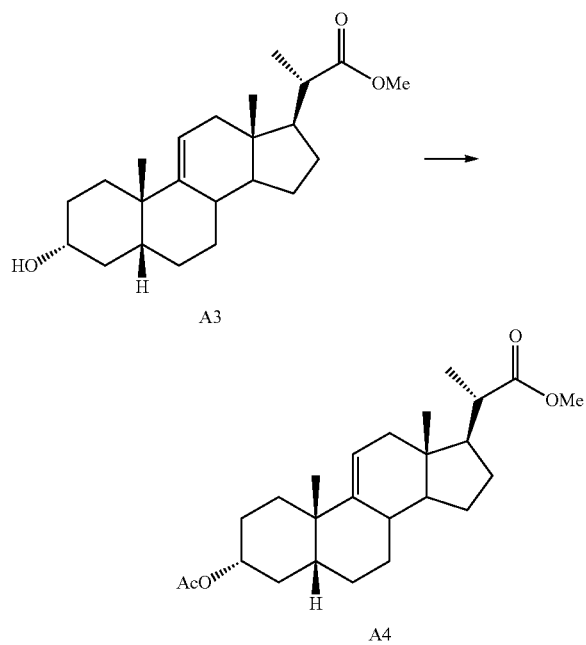

A3 27.62 g (76.61 mmol) (10 g) was dissolved in DCM (70 ml) at room temperature. Then, Triethylamine 50 ml (6.66 eqv), Acetic anhydride 8.85 g (3.33 eq) and DMAP (3.40 g) were added, keeping the temperature below 10° C. The mixture stirred until reaction was complete. The organic phase was concentrated under reduced pressure and the solid was suspended in 60 mL of DCM and then washed with a solution of 1M HCl. The solvent was evaporated under reduced pressure thereby yielding 32.29 g of A4. $^1$H NMR (400 MHz, CDCl$_3$): δ 0.58 (s, 3H); 1.04 (s, 3H); 1.16 (d, 3H); 1.99 (s, 3H); 2.41 (m, 2H); 3.63 (s, 3H); 4.71 (m, 1H); 5.31 (dd, 1H).

$^1$H NMR (400 MHz, CDCl$_3$): δ 5.31 (s, 1H); 3.60 (s, 3H); 2.00 (m, 3H); 1.17 (d, 3H); 0.59 (s, 3H).

Example 7

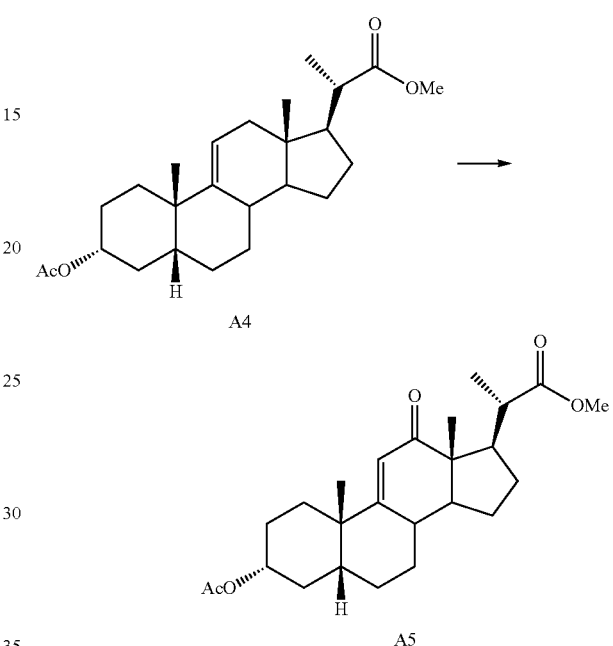

27 g of compound A4 (64.5 mmol) was suspended in 300 ml of AcOH and then anhydrous CrO$_3$ (27.73 g, 4.30 eqv) was added. The suspension was heated at 60° C. The reaction mixture was stirred for 0.5 h until the reaction was complete. Then, the mixture was poured over 250 mL of water and a precipitate was formed. The organic phase was washed with water. The operation was repeated two more times. The organic phase were concentrated until an oily residue was obtained. The residue was purified on silica gel yielding 13.05 g of pure A5.

$^1$H NMR (400 MHz, CDCl$_3$): δ 0.84 (s, 3H); 1.17 (s, 3H); 1.30 (d, 3H); 1.98 (s, 3H); 3.63 (s, 3H); 4.72 (m, 1H); 5.72 (s, 1H).

Example 8

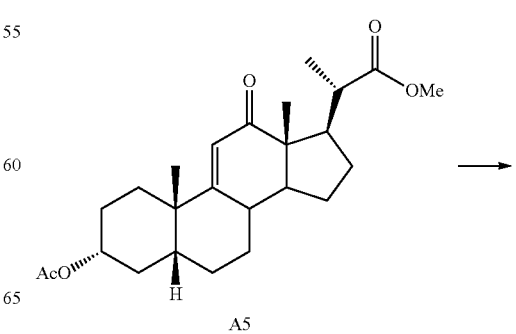

A5

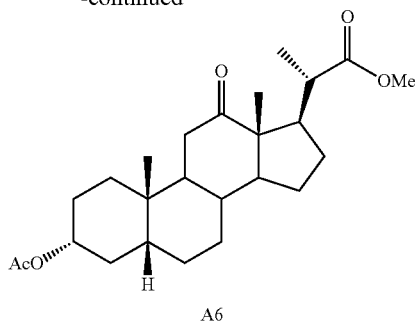

A6

11 g of A5 (28.31 mmol) was dissolved in 65 ml of AcOEt followed by addition of 2.75 g dry Pd/C 10% (25% weight). The reaction mixture was stirred at 70° C. and hydrogenated (4.1 atm) overnight. The mixture was filtered through Celite® and the solvent was evaporated under vacuum, thereby yielding 11.02 g of A6 (a white solid. ¹H NMR (400 MHz, CDCl₃): δ 0.97 (s, 3H); 1.00 (s, 3H); 1.15 (d, 3H); 2.00 (s, 3H); 2.46 (m, 2H); 3.63 (s, 3H); 4.68 (m, 1H).

Example 9

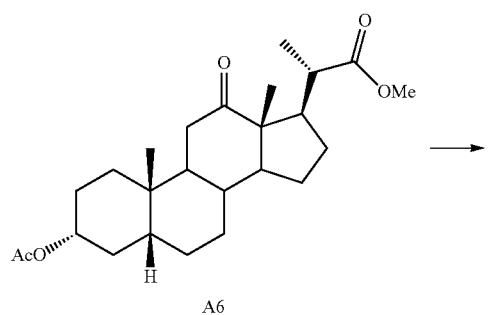

A6

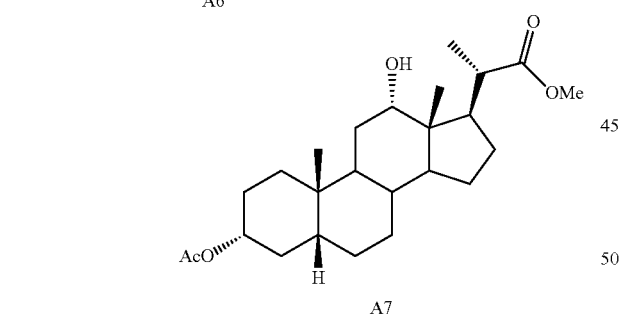

A7

11.02 g of A6 (26.30 mmol) was dissolved and stirred in THF (40 ml) under an inert atmosphere. The solution was cooled at 0-5° C. LiAlH(OtBu)₃ (1.5 eqv, 10.0 g, 39.45 mmol) was added dropwise (exothermic reaction). The mixture was stirred at room temperature until the reaction was complete. The mixture was cooled at 0-5° C. and was then quenched by adding an aqueous solution of 1M HCl. The aqueous phase was extracted with EtOAc and the organic phase was washed with a solution of NaHCO₃. The solvent was evaporated under reduced pressure, thereby yielding 11.16 g of A7. ¹H NMR (400 MHz, CDCl₃): δ 0.66 (s, 3H); 0.89 (s, 3H); 1.20 (d, 3H); 2.00 (s, 3H); 3.62 (s, 3H); 3.92 (m, 1H); 4.72 (m, 1H).

Example 10

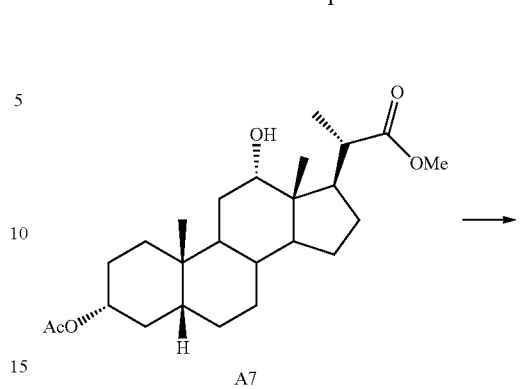

A7

A7A 3.00 g of A7 (7.13 mmol) was dissolved and stirred in a mixture of THF (30 ml) and MeOH (30 ml) under an inert atmosphere at room temperature. LiOH (4M, 30 ml) was added. The solution was heated at 60° C. The mixture was stirred until the reaction was complete (6 h). The mixture was cooled at room temperature. The solvent was evaporated and was quenched by adding an aqueous solution of HCl 2N until acidic pH. The precipitate was filtered off as a palid yellow solid, washed with water and EtOAc, and then dried under vacuum yielding 2.53 g of A7A.

Example 11

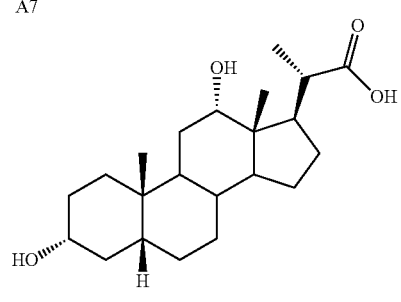

A7

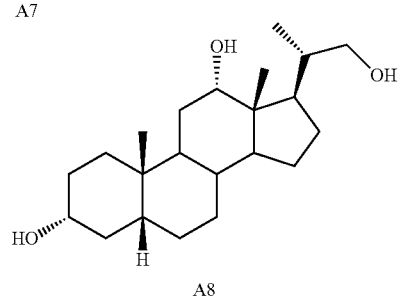

A8

0.3 g of A7 (0.71 mmol) was dissolved and stirred in dry THF (7 ml) under an inert atmosphere. The solution was cooled at 0-5° C. LiAlH$_4$ (0.06 g, 1.49 mmol) was added dropwise (exothermic reaction). The mixture was stirred at room temperature until the reaction was completed. The mixture was cooled at 0-5° C. and was quenched by addition Na$_2$SO$_4$.10H$_2$O. The precipitate was filtered off and washed with THF. The solvent was evaporated under reduced pressure and the solid obtained was washed with EtOAc, thereby yielding 0.198 g of A8.

$^1$H NMR (400 MHz, CDCl$_3$): δ 3.95 (t, J=2.8 Hz, 1H), 3.56 (dd, J=10.5, 3.4 Hz, 1H), 3.50 (td, J=11.1, 5.5 Hz, 1H), 3.21 (dd, J=10.5, 7.7 Hz, 1H), 1.95-1.70 (m, 6H), 1.66-1.22 (m, 16H), 1.19-1.10 (m, 2H), 1.07 (d, J=6.6 Hz, 3H), 1.02-0.94 (m, 1H), 0.92 (s, 3H), 0.72 (s, 3H).

Example 12

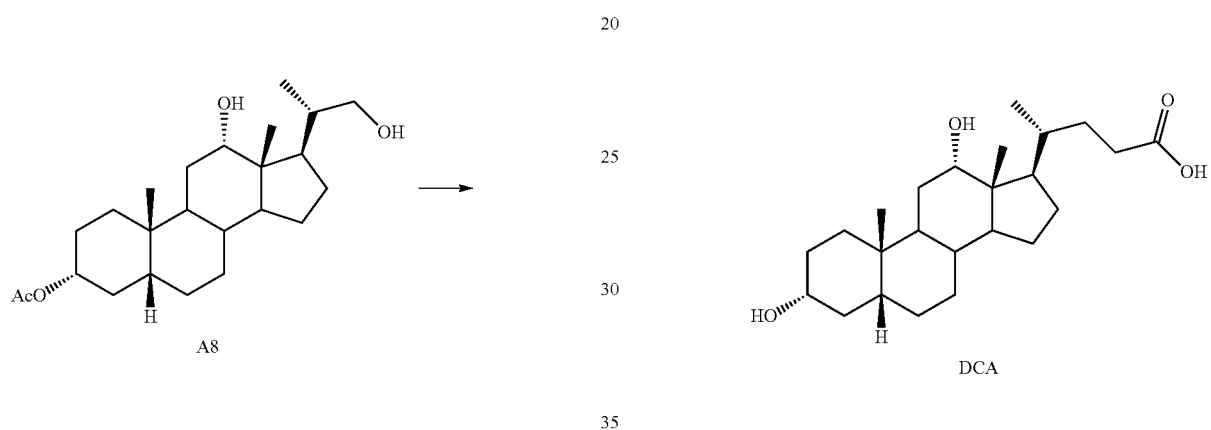

A8

A9

0.025 g of A8 (0.078 mmol) was dissolved and stirred in DCM (2 ml). CBr$_4$ (2.4 eqv, 0.062 g, 0.09 mmol) and triphenylphosphine (PPh$_3$, 2.5 eqv, 0.051 g, 2.5 mmol) was added. The solution was heated under reflux. The mixture was stirred until the reaction was completed. The mixture was cooled at room temperature. The residue was purified on silica gel yielding 0.05 g of A9.

$^1$H NMR (400 MHz, CDCl$_3$): δ 3.93 (t, J=2.8 Hz, 1H), 3.63-3.52 (m, 1H), 3.48 (dt, J=5.9, 2.9 Hz, 1H), 3.29 (dd, J=9.7, 6.5 Hz, 1H), 1.90-1.15 (m, 23H), 1.11 (d, J=6.5 Hz, 3H), 0.94 (ddd, J=12.6, 9.9, 2.5 Hz, 1H), 0.87 (s, 3H), 0.67 (s, 3H).

Example 13

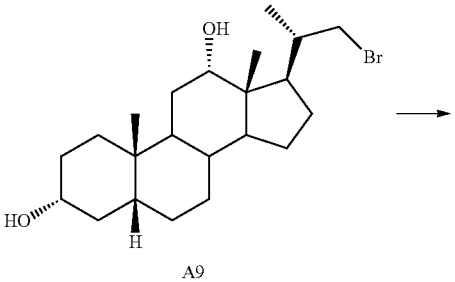

A9

DCA 0.5 g of NaH 60% (12.5 mmol) was dissolved and stirred in dry DMF (10 ml) under an inert atmosphere. Diethyl malonate (2.0 g, 12.48 mmol) dissolved in 3.0 ml of DMF was added dropwise. The solution was heated and stirred until the mixture was turned clear. The mixture was cooled at 40° C. A9 (5.12 g, 12.4 mmol) dissolved in 3.0 ml of DMF was added. The solution was heated at 60° C. The mixture was quenched by addition of water (15 ml). The aqueous phase was extracted with EtOAc. The solvent was evaporated under reduced pressure and the residue was suspended in an aqueous solution of KOH 2.8 M (10.0 ml). The solution was heated under reflux. Water (10 ml) was added and the organic solvent was evaporated under reduced pressure. The aqueous phase was acidified by adding 2N HCl and was extracted with EtOAc. The solvent was evaporated under reduced pressure and the residue was suspended in a mixture of dioxane (5 ml) and 12N HCl (10 ml). The mixture was heated under reflux for 24 hours. The mixture was cooled at room temperature and was extracted with EtOAc. The organic phases were mixed and evaporated under reduced pressure. The residue was purified on silica gel thereby yielding 3.1 g of DCA.

Example 14

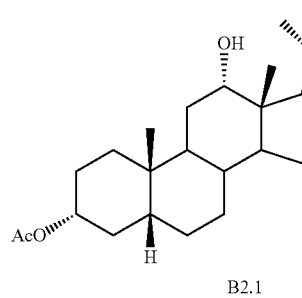

B2.1

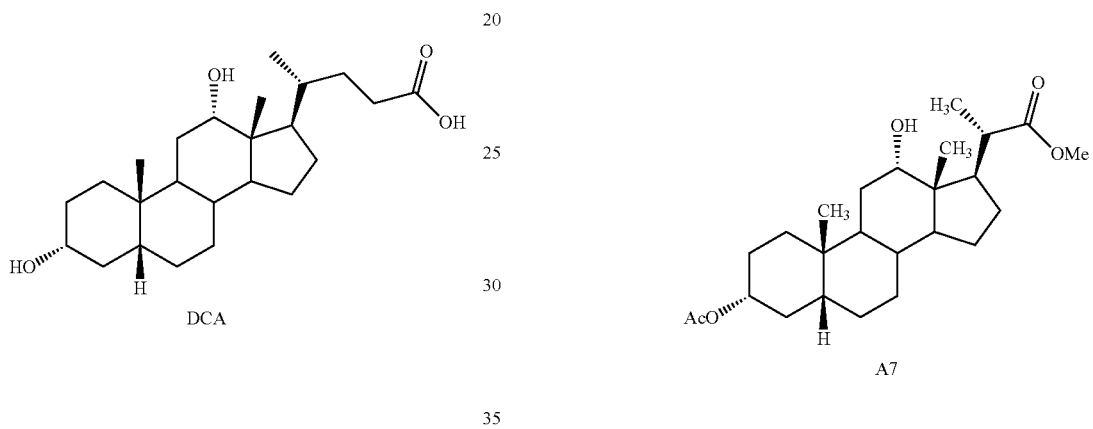

DCA 0.42 g of B2.1 (0.92 mmol) was dissolved and stirred in THF (8 ml). Water (8 ml) was added and stirred at room temperature. A solution of LiOH 4M (2.0 ml) was added. The mixture was heated at 50° C. and stirred overnight. The mixture was poured over water. The aqueous phase was extracted with EtOAc. The organic phase was washed with an aqueous solution of 2N HCl. The aqueous phase was extracted with EtOAc and the combined organic layers were evaporated under reduced pressure, thereby yielding 0.38 g of DCA. $^1$H NMR (400 MHz, CDCl$_3$): δ 3.94 (t, J=2.7 Hz, 1H), 3.58-3.45 (m, 1H), 2.41-2.11 (m, 2H), 1.99-1.71 (m, 7H), 1.67-1.04 (m, 19H), 0.99 (d, J=6.4 Hz, 3H), 0.92 (s, 3H), 0.70 (s, 3H)

Example 15

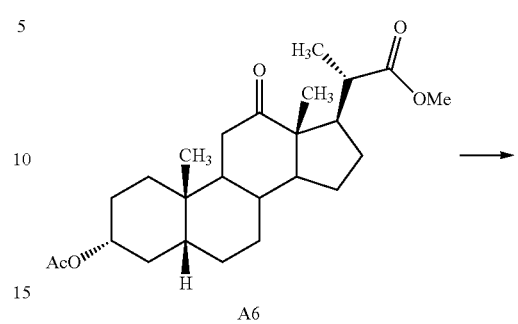

A6

A7

10.5 g of A6 (24.0 mmol) were dissolved and stirred in THF (137 ml) under inert atmosphere. The solution was cooled at −40° C. LiAl(OtBu)$_3$H (1.1 eq, 6.6 g, 26.0 mmol) was added dropwise (exothermic reaction). The mixture was stirred at −20° C. until the reaction was complete. The solvent was evaporated under reduced pressure then the mixture was cooled at 0/5° C. The solid was filtered off, washed with water and dried, affording 10.55 g of compound A7.

Example 16

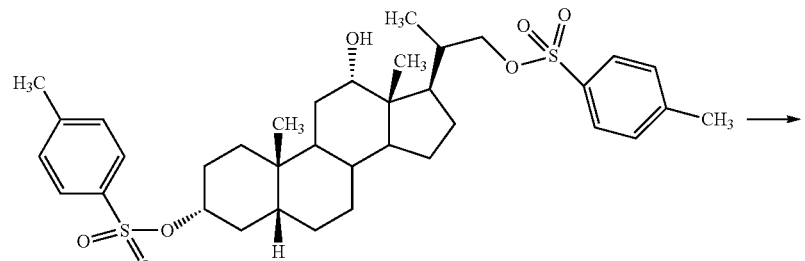

A9.1

-continued

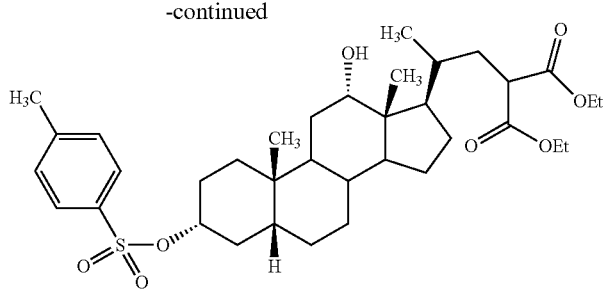

A10.1

1.6 g of NaH 60% (39.5 mmol) were dissolved and stirred in dry DMF (0.5 ml) under inert atmosphere. Diethyl malonate (6.2 ml, 4.02 mmol) dissolved in 0.5 ml of DMF were added dropwise. A suspension of the steroid intermediate (6.1 g, 9.8 mmol) in 1.0 ml DMF were added dropwise. The solution was heated and was stirred at 60° C. The mixture was quenched by adding water (15 ml). The aqueous phase was extracted with EtOAc. The solvent was evaporated under reduced pressure. The residue was purified by chromatography on silica gel.

Example 17

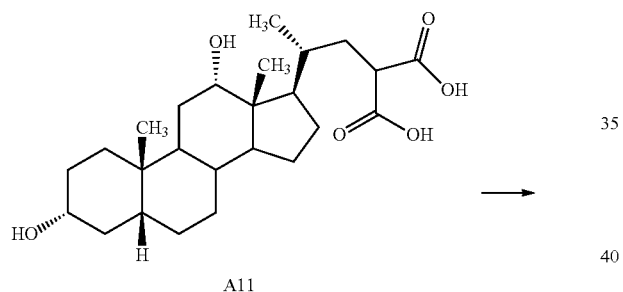

A11

↓

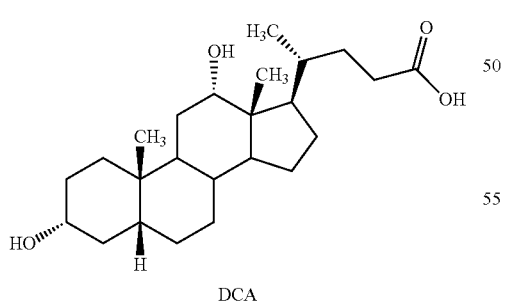

DCA

A11 (1.8 g, 4.12 mmol) were suspended in 108 ml of Xiylene. The suspension was heated under reflux. The mixture was slowly cooled at 20/25° C. Water (54 ml) and EtOAc (270 ml) were added. The aqueous phase was cooled at 10° C. and acidified by adding HCl 2N. The mixture was stirred and the solid was filtered off, washed with water and dried, affording 1.04 g of Deoxycholic acid.

Example 18

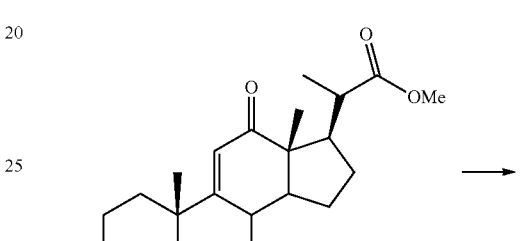

A5

→

A5.1

4.00 g of A5 (9.6 mmol) was dissolved and stirred in MeOH (150 ml) under an inert atmosphere at room temperature. NaOH 20% (40 ml, 22 mmoles) was added. The solution was heated at reflux. The mixture was stirred until the reaction was complete (3 h). The mixture was cooled at room temperature. The solvent was evaporated and was quenched by adding an aqueous solution of HCl 6N until acidic pH. The precipitate was filtered off as a solid, washed with water and EtOH, and then dried under vacuum yielding 3.4 g (95%) of A5.1.

$^1$H-RMN (400 MHz, DMSO-d6) δ=0.57 (s, 3H); 0.81 (s, 3H); 1.09 (d, J=6 Hz, 3H); 3.71 (m, 1H).

Example 19

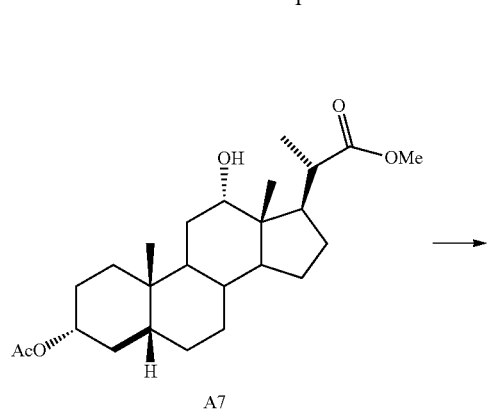

A7

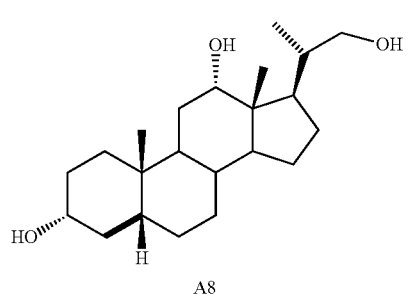

A8

3.0 g of A7 (7.14 mmol) was dissolved and stirred in THF (75 ml) under inert atmosphere. The solution was cooled at 0-5° C. and LiAlH$_4$ (1.1 g, 28.6 mmol) was added slowly (exothermic reaction). The mixture was stirred at room temperature then heated under reflux until the reaction was complete. The mixture was cooled at room temperature and was hydrolyzed slowly with a solution of water (1.1 ml), NaOH (20%) 1.1 ml and water (3.3 ml). The white solid obtained was filtered off and was washed THF (150 ml). The organic phase was dried with anhydrous Magnesium sulfate. The solvent was evaporated under reduced pressure, yielding 2.3 g (92%) of A8.

Example 20

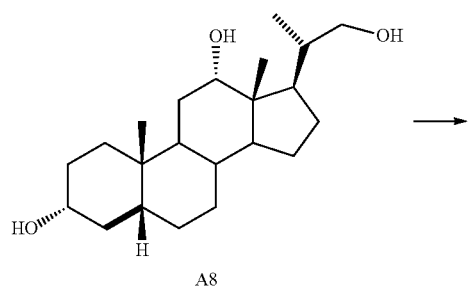

A8

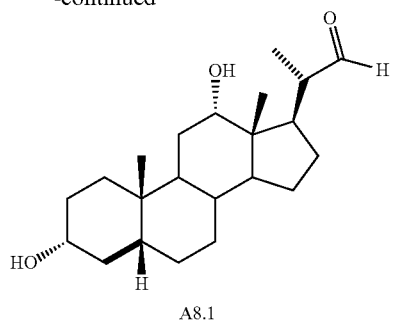

A8.1

0.2 g of compound A8 (0.57 mmol) was suspended in a mixture of DCM (6.0 ml) and ACN (6.0 ml) under inert atmosphere and then Dess-Martin Periodinane reagent (0.24 g, 0.57 mmol) and 4-methylmorpholine 4-oxide (11 mg, 0.07 mmol) were added. The suspension was stirred at room temperature until the reaction was complete. Then, a solution of Na$_2$S$_2$O$_3$ (1M, 50 mL) was added. The aqueous phase was extracted with DCM (3×50 ml) and then was washed with brine. The organic phase were concentrated until a solid was obtained, yielding 0.25 g of A8.1.

$^1$H NMR (400 MHz, CDCl$_3$): δ 9.7 (d, 1H); 9.5 (d, 1H); 3.6 (m, 1H); 3.4 (bs, 1H); 2.3 (qd, J=9 Hz, 1H).

Example 21

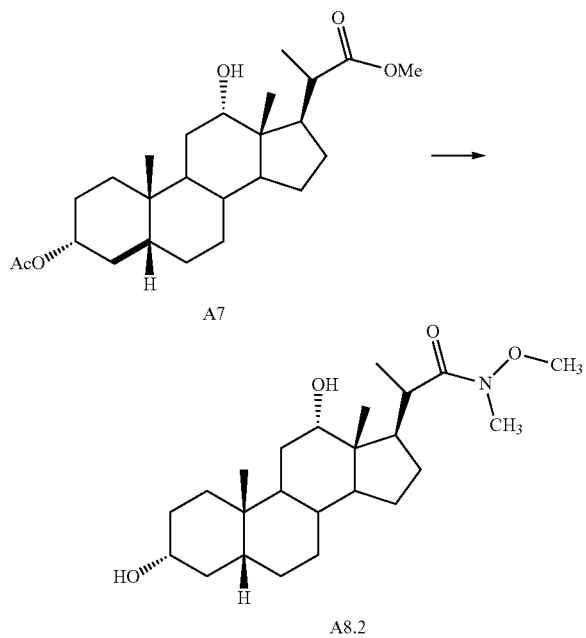

A7

A8.2

2.00 g of A7 (4.76 mmol) was dissolved and stirred in MeOH (100 ml) under inert atmosphere at room temperature. NaOH 20% (20 ml) was added. The solution was heated at 80° C. The mixture was stirred until the reaction was complete (3 h). The mixture was cooled at room temperature. The solvent was evaporated and the mixture was quenched by adding an aqueous solution of HCl 6N until acidic pH. The precipitate was filtered off as a solid, washed with water and MeOH, and then dried under vacuum yielding 1.4 g (80%) of acid intermediate.

9.0 g of intermediate acid compound (25 mmol), DCC (6.2 g, 30 mmol), DMAP (3.7 g, 30 mmol) and N,O-dimethylhydroxylamine hydrochloride (4.9 g, 50 mmol) were dissolved in DCM (250 ml) under inert atmosphere. Et$_3$N (10 ml) was added and the suspension was stirred at room temperature until the reaction was complete. Then, the organic phase was washed with brine. The organic phase was concentrated until a solid was obtained. The solid was purified by column chromatography (AcOEt/Heptane), yielding 5.9 g of A8.2.

$^1$H NMR (400 MHz, CDCl$_3$): δ 3.9 (bs, 1H); 3.66 (s, 3H); 3.61 (m, 1H); 3.15 (s, 3H); 2.4 (q, J=9 Hz, 1H).

Example 22

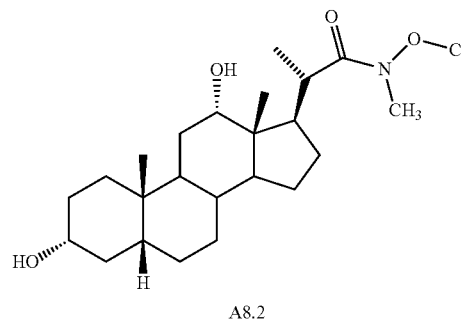

A8.2

2.5 g of A8.2 (6.14 mmol) was dissolved and stirred in THF (25 ml) under inert atmosphere. The solution was cooled at 0-5° C. and was added slowly (exothermic reaction) to a solution of LiAlH$_4$ (0.36 g, 9.2 mmol) in THF (75 ml). The mixture was stirred at 0-5° C. until the reaction was complete. The mixture was hydrolyzed slowly with a solution of water (0.25 ml), NaOH (20%) 0.25 ml and water (0.75 ml). The white solid obtained was filtered off and was washed THF (100 ml). The organic phase were concentrated and was purified by column chromatography (AcOEt/Heptane), yield 85% of A8.2.

Example 23

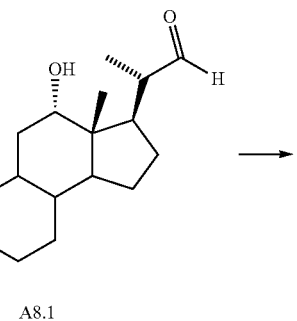

A8.1

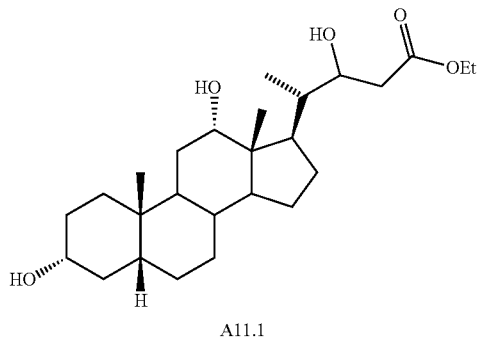

A11.1

0.26 g of Zn (4.1 mmol) was suspended in THF under inert atmosphere. Trimethylchlorosilane (0.1 mmol) were added. The suspension was stirred at heated under reflux 1 hour. Then, a solution of 0.2 g of A8.1 (0.57 mmol) and Ethyl Bromoacetate 0.3 ml (2.85 mmol) in THF (20 ml) were added. The mixture was stirred at heated under reflux until the reaction was complete. The mixture was cooled at room temperature. The solvent was evaporated and the mixture was quenched by adding an aqueous saturated solution of NH$_4$C$_1$ (50 ml). EtOAc (75 ml) was added. The organic phase was washed with an aqueous saturated solution of NaCl. The organic phase were concentrated and the solid was purified by column chromatography (EtOAc/Heptane).

$^1$H NMR (400 MHz, CDCl$_3$): δ 4.35 (dt, J=9 Hz, J=3 Hz, 1H); 4.55 (q, J=7.5 Hz, 2H); 3.35 (m, 1H); 2.7 (dd, J=17 Hz, J=9 Hz, 1H); 2.75 (dd, J=17 Hz, J=3 Hz, 1H).

Example 24

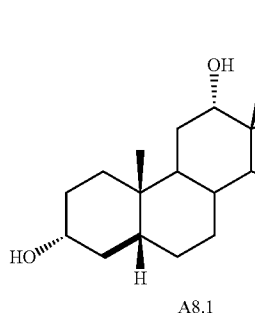

A8.1

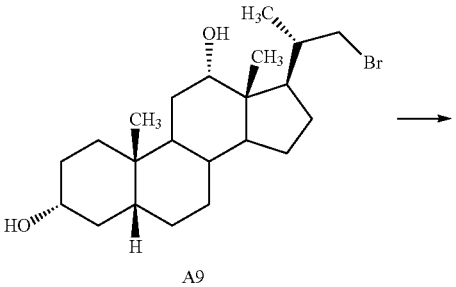

A9

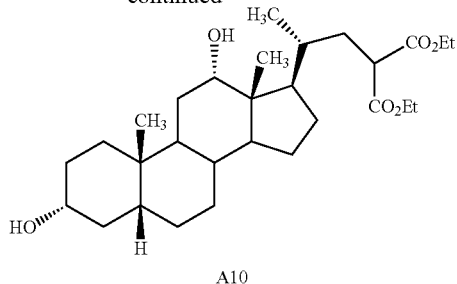

A10

0.41 g of EtONa (0.60 mmol) was dissolved and stirred in EtOH (2 ml) under an inert atmosphere and was cooled at 0° C. Diethyl malonate (0.97 g, 0.60 mmol) was added to the mixture. The mixture was heated at room temperature and A9 (0.20 g, 0.48 mmol) were added. The solution was heated at 90° C. The mixture was quenched by addition of water (5 ml). The aqueous phase was extracted with EtOAc. The organic phases were evaporated under reduced pressure. The residue was purified on silica gel thereby yielding 0.12 g of A10.

Example 25

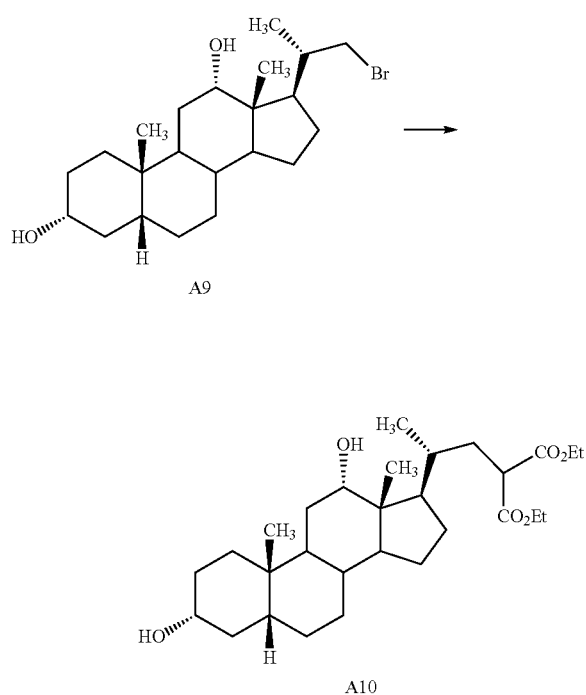

A9

A10

0.15 g of NaH 60% (3.87 mmol) was dissolved and stirred in DMF (2 ml) under an inert atmosphere and was cooled at 0° C. Diethyl malonate (0.59 ml, 3.87 mmol) was added to the mixture. The mixture was heated at room temperature and A9 (0.40 g, 0.96 mmol) were added. The solution was heated at 60° C. The mixture was poured into a solution of NaCl 20% (30 ml). The aqueous phase was extracted with EtOAc. The organic phases were evaporated under reduced pressure. The residue was purified on silica gel thereby yielding 0.76 g of A10.

Example 26

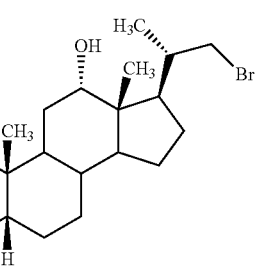

A9

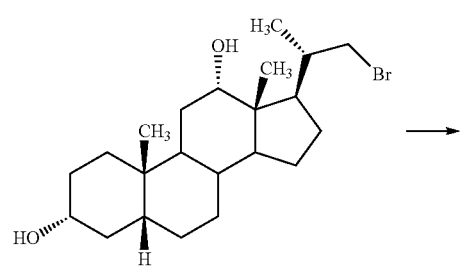

A11

5.86 g of NaH 60% (146.4 mmol) was dissolved and stirred in dry DMF (75 ml) under an inert atmosphere cooled at 0° C. Diethyl malonate (23.4 g, 146.4 mmol) was added dropwise. The solution was stirred until the mixture was turned clear. A9 (15.13 g, 36.6 mmol) dissolved in 75.0 ml of DMF was added. The solution was heated at 60° C. The mixture was quenched with a solution of NaCl 20% (1200 ml). The aqueous phase was extracted with EtOAc. The solvent was concentrated under reduced pressure and the mixture was cooled at room temperature and stirred until solid was precipitated. The solid was filtered off and dried, yielding 25.3 g of A11.

$^1$H NMR (400 MHz, CDCl$_3$): δ 3.95-3.93 (m, 1H), 3.57-3.46 (m, 1H), 3.39 (dd, J=11.1, 3.5 Hz, 1H), 2.12 (t, J=11.4 Hz, 1H), 1.96-1.04 (m, 25H), 1.00 (d, J=7.5 Hz, 3H), 0.91 (s, 3H), 0.68 (s, 3H).

Example 27

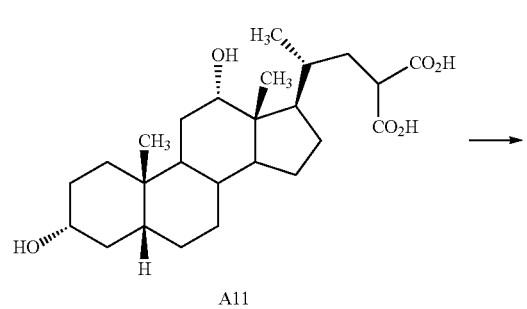

A11

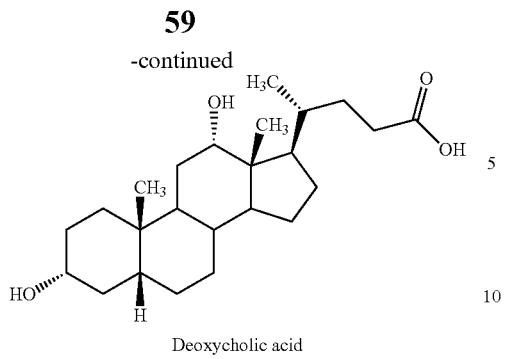

Deoxycholic acid

A11 (3.0 g, 0.76 mmol) were suspended in 90.0 ml of NaCl 20%. The suspension was heated at reflux for 60 hours. The mixture was cooled to room temperature. The solid was filtered off and dried, yielding 2.48 g of DCA.

Example 28

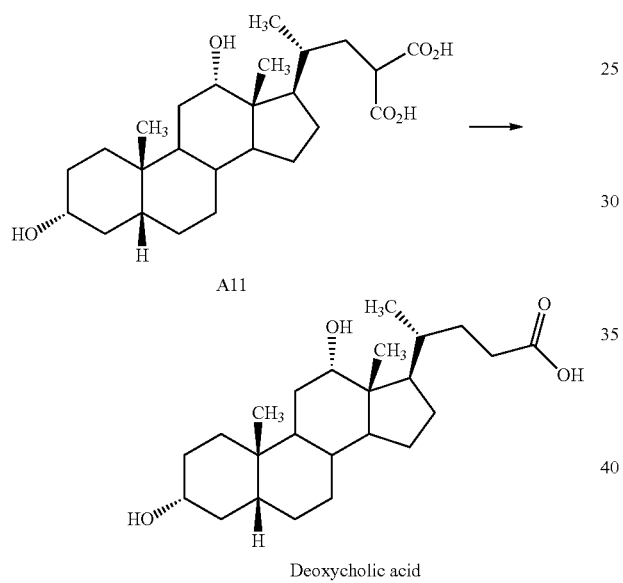

A11

Deoxycholic acid

A11 (0.3 g, 0.076 mmol) were suspended in 9.0 ml of a solution of aqueous NaH$_2$PO$_3$ (pH 4.55). The suspension was heated at reflux for 70 hours. The mixture was cooled at room temperature. The solid was filtered off and dried, yielding 0.22 g of DCA.

Example 29

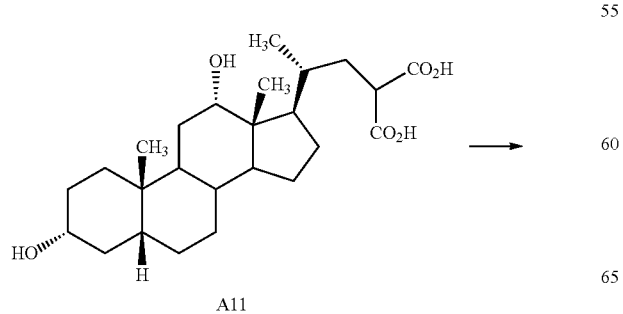

A11

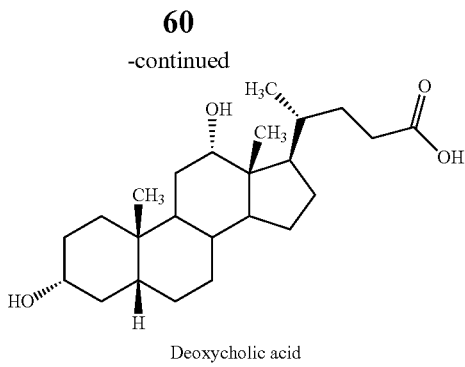

Deoxycholic acid

A11 (0.3 g, 0.076 mmol) were suspended in 9.0 ml of water in a pressure vessel and was closed. The suspension was heated at reflux for 80 hours. The mixture was cooled to room temperature. The solid was filtered off and dried, yielding 0.23 g of DCA.

Example 30

A8

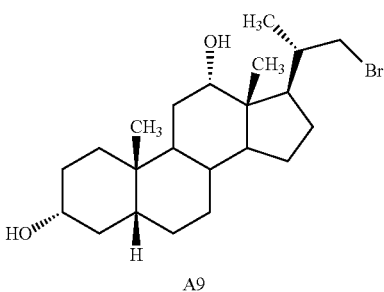

A9

0.05 g of A8 (0.14 mmol) was dissolved and stirred in ACN (1 ml), the mixture is cooled at 0° C. A solution of PPh$_3$Br$_2$ (0.105 g, 0.24 mmol) in ACN (1 ml) was added dropwise. The mixture was stirred until the reaction was completed. The mixture was cooled at room temperature. The residue was purified on silica gel yielding 0.04 g of A9.

Example 31

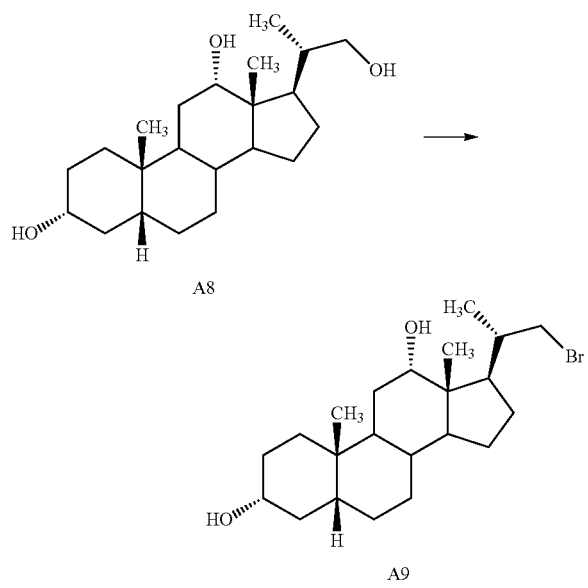

0.05 g of A8 (0.14 mmol) was dissolved and stirred in DCM (2 ml), under an inert atmosphere and cooled to −40° C. 0.4 ml of a solution of TPP (0.077 g, 1.75 eq) in DCM (8 ml) was added dropwise. 0.4 ml of a solution of $Br_2$ (0.04 g, 1.75 eq) in DCM (8 ml) was added dropwise. The mixture was stirred until the reaction was completed. The mixture was allowed to reach room temperature. The residue was purified on silica gel yielding 0.05 g of A9.

Example 32

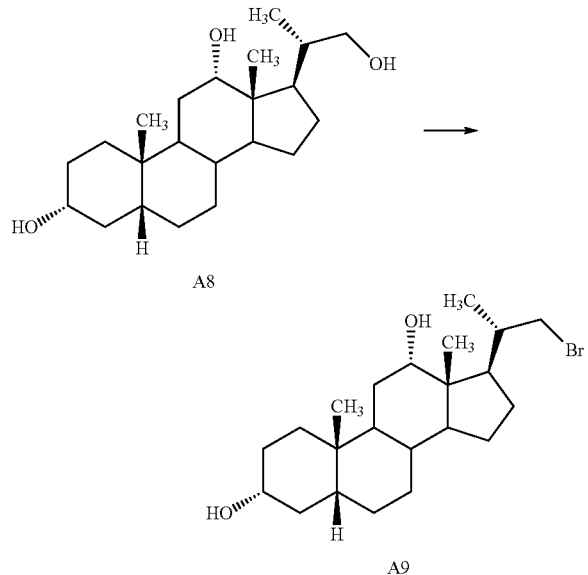

0.05 g of A8 (0.14 mmol) was dissolved and stirred in ACN (1 ml), and cooled to 0° C. A solution of $PPh_3Br_2$ (0.105 g, 0.24 mmol) in ACN (1 ml) was added dropwise. The mixture was stirred until the reaction was completed. The mixture was warmed to room temperature. The residue was purified on silica gel yielding 0.04 g of A9.

Example 33

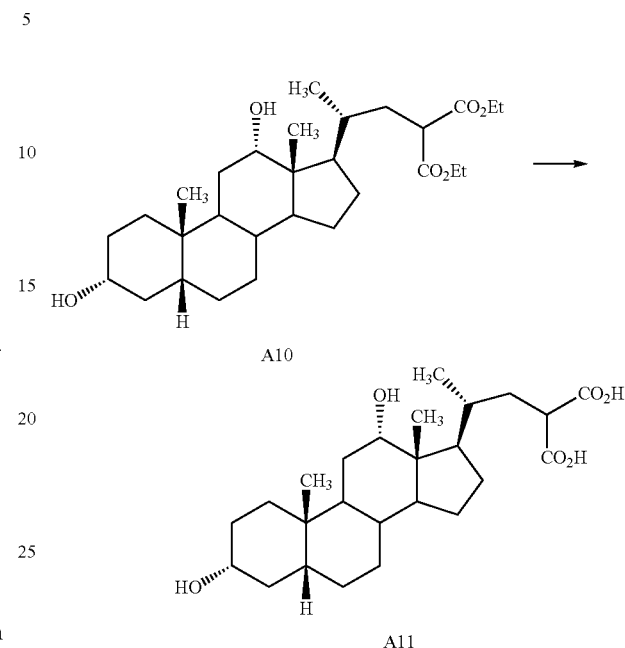

5.0 g of A10 (10.15 mmol) was dissolved in EtOH (25 ml) and stirred at room temperature. NaOH 4M (40 ml) was added and the mixture was stirred. The organic solvent was concentrated under reduced pressure. Water (30 ml) wad added dropwise and a solid was obtained. The aqueous phase was washed with DCM (150 ml). The aqueous phase was acidified with HCl 2 N (until pH 1). The mixture was stirred at room temperature and a solid was obtained. The solid was filtered off and dried, yielding 3.5 g of A11.

Example 34

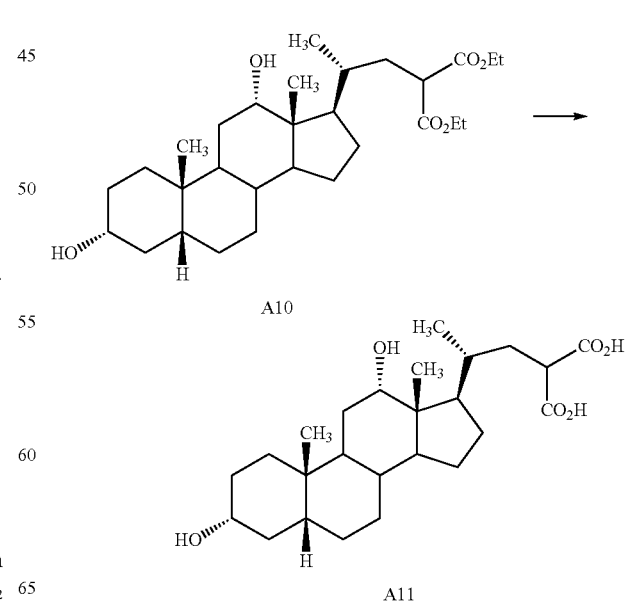

5.0 g of A10 (10.15 mmol) was dissolved in EtOH (25 ml) and stirred at room temperature. LiOH 4M (40 ml) was added and the mixture was stirred at 40° C. until the reaction was completed. The organic solvent was concentrated under reduced pressure. Water (500 ml) and DCM (150 ml) was added. The aqueous phase was separated and was acidified with HCl 2 N (until pH 1). The mixture was stirred at room temperature and a solid was obtained. The solid was filtered off and dried, yielding 4.3 g of A11.

Example 35

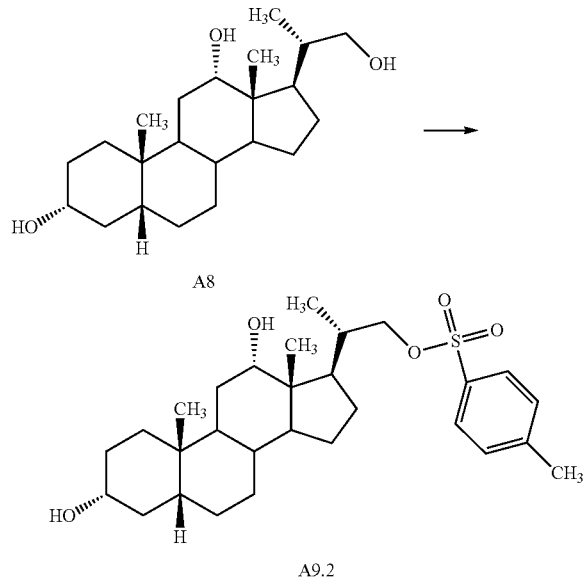

0.05 g of A8 (0.14 mmol) was dissolved and stirred in DCM (1 ml), the mixture is cooled at 0° C. TsCl (0.05 g, 0.28 mmol) and DMAP (0.03 g, 0.28 mmol) were added. The suspension was stirred until the reaction was completed. The mixture was allowed to reach room temperature. The residue was purified on silica gel yielding 0.04 g of A9.2.

EMBODIMENTS OF THE INVENTION

A. A process for the preparation of deoxycholic acid (DCA) or a pharmaceutically acceptable salt thereof, comprising the following steps:

I) providing a compound of the general formula SM:

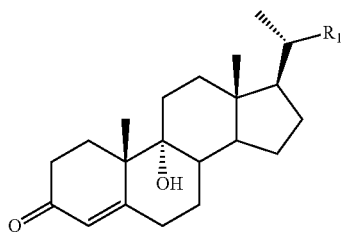

II) reducing the compound of the general formula SM to obtain an intermediate of the general formula INT 1:

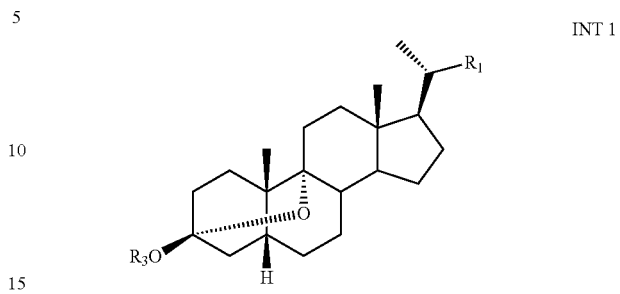

III) converting the intermediate of the general formula INT 1 into an intermediate of the general formula INT 2:

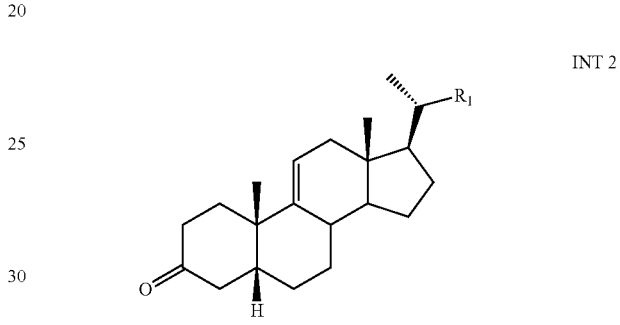

IVa) reducing the intermediate of the general formula INT 2 into an intermediate of the general formula INT 3:

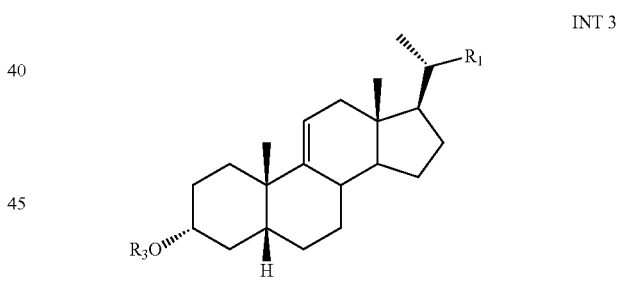

followed by converting the intermediate of the general formula INT 3 into an intermediate of the general formula INT B:

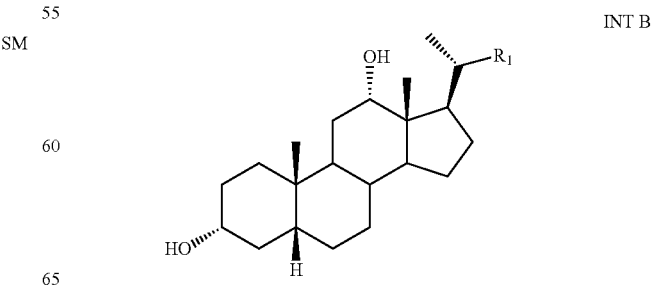

or

IVb) converting the intermediate of the general formula INT 2 into an intermediate with the general formula INT B:

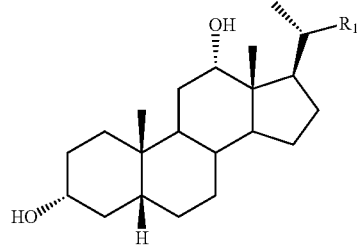

INT B

V) converting the intermediate of the general formula INT B into deoxycholic acid (DCA):

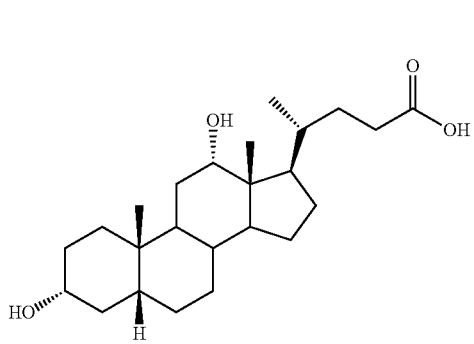

DCA

VI) optionally converting deoxycholic acid to a pharmaceutically acceptable salt thereof, wherein $R_1$ is $COOR_2$, $CH_2OH$, $CH_2OP$, $CH_2X$, $CH_2CHO$, $CH_2$—$CH_2$—OH, $CH_2$—$CH_2OP$, or $CH_2$—$CH_2X$ or $CH_2$—$CH_2$—CHO;

$R_2$ is H or a linear or branched $C_1$-$C_6$-alkyl group;

P is an alcohol protection group;

$R_3$ either P or $R_2$; and

X is a halogen atom.

B. The process according to embodiment A, comprising the following steps:

i) providing a compound of the general formula SM-a:

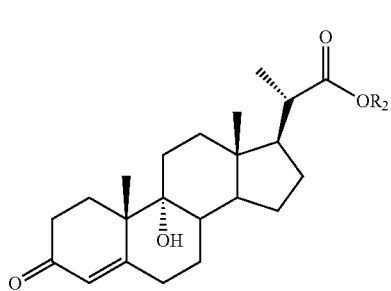

SM-a ii) reducing the compound of the general formula SM-a to obtain an intermediate of the general formula Int A1:

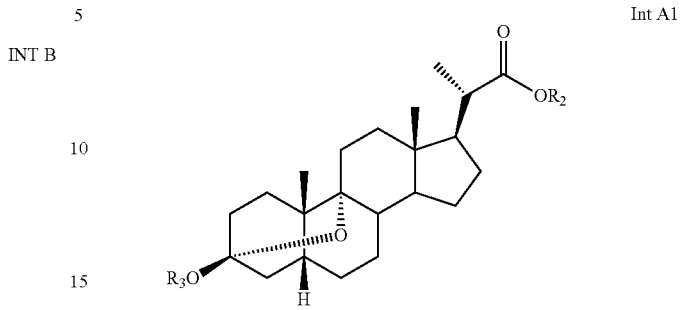

Int A1 iii) converting the intermediate of the general formula Int A1 into an intermediate of the general formula Int A2:

Int A2 iv) reducing the intermediate of the general formula Int A2 into an intermediate of the general formula Int A3:

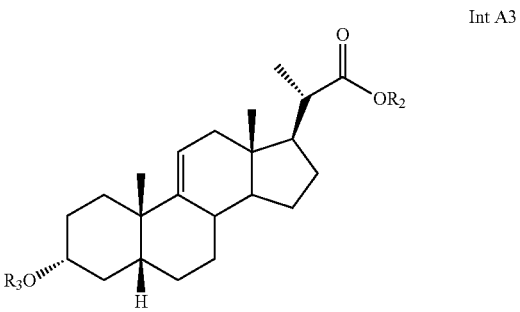

Int A3 v) oxidising the intermediate of the general formula Int A3 into an intermediate of the general formula Int A5:

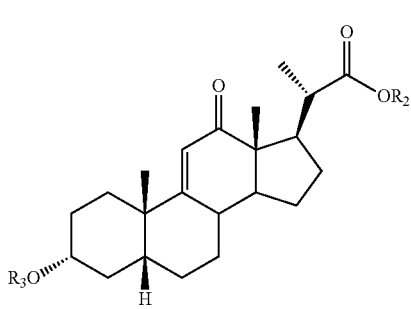

Int A5 vi) reducing the intermediate of the general formula Int A5 into an intermediate of the general formula Int A6:

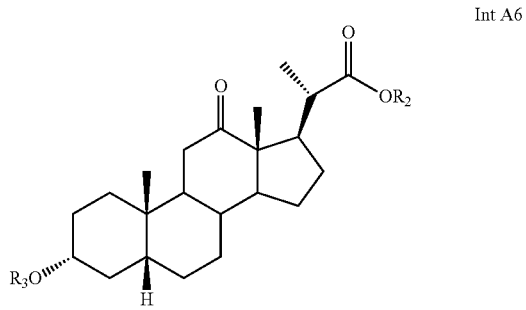

vii) reducing the intermediate of the general formula Int A6 into an intermediate of the general formula Int A7:

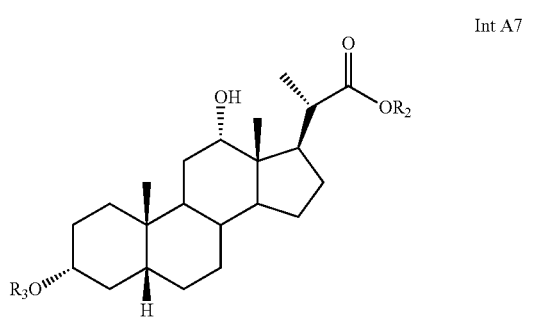

viii) reducing the compound of the general formula Int A7 into an intermediate of the general formula Int A8:

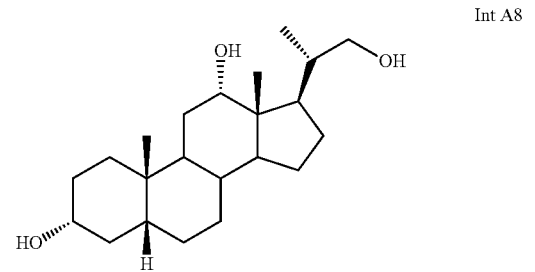

ix) elongating the carbon chain of the compound of the general formula Int A8 to obtain deoxycholic acid (DCA):

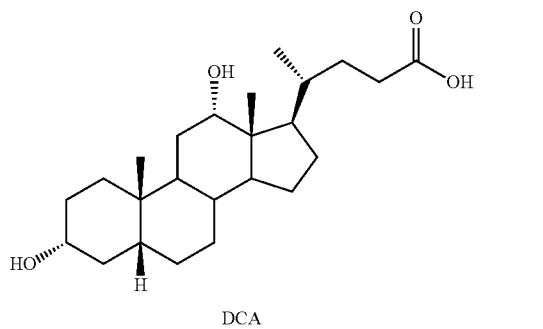

x) optionally converting deoxycholic acid to a pharmaceutically acceptable salt thereof, wherein
$R_2$ is H or a linear or branched $C_1$-$C_6$-alkyl group;
$R_3$ is H, $R_2$ or an alcohol protection group.

C. The process according to embodiment A or B, wherein $R_2$ is selected from the group consisting of methyl, ethyl, n-propyl and isopropyl.

D. The process according to embodiment C, wherein $R_2$ is methyl or ethyl.

E. The process according to embodiment D, wherein $R_2$ is methyl.

F. The process according to any of the preceding embodiments, wherein $R_3$ is selected from the group consisting of trimethylsilyl ether (TMS), triethylsilyl ether (TES), triisopropylsilyl ether (TIPS), tert-butyldimethylsilyl ether (TBS, TBDMS), tert-butyldiphenylsilyl ether (TBDPS), acettyl (Ac, $COCH_3$), benzoyl (Bz), benzyl ether (Bn), 4-methoxybenzyl ether (PMB), 2-naphthylmethyl ether (Nap), methoxymethyl acetal (MOM), 2-methoxyethoxy-methyl ether (MEM), ethoxyethyl acetal (EE), methoxypropyl acetal (MOP), benzyloxymethyl acetal (BOM), tetrahydropyranyl acetal (THP), 2,2,2-trichloro-ethyl carbonate (Troc), methyl ether, dimethoxytrityl (DMT), methoxytrityl (MMT), methylthiomethyl ether, pivaloyl (Piv), tetrahydropyranyl (THP), triphenylmethyl (trityl, Tr), and tosyl (Ts).

G. The process according to embodiment F, wherein $R_3$ is selected from the group consisting of Ac, TBDMS and Ts.

H. The process according to embodiment G, wherein $R_3$ is Ac.

I. The process according to embodiment A or B, wherein $R_2$ is methyl and $R_3$ is Ac.

J. The process according to embodiment J, wherein $R_3$ is $R_2$, and $R_2$ is as defined in any of embodiments B-D.

K. A process for the preparation of deoxycholic acid (DCA) or a pharmaceutically acceptable salt thereof, comprising the following steps:

I) providing a compound of the general formula INT 3:

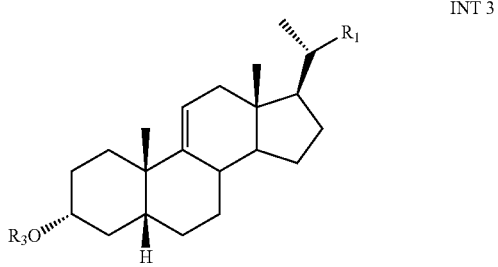

II) converting the intermediate of the general formula INT 3 into an intermediate of the general formula INT B:

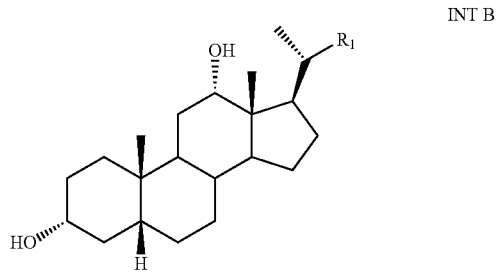

III) converting the intermediate of the general formula INT B into deoxycholic acid (DCA):

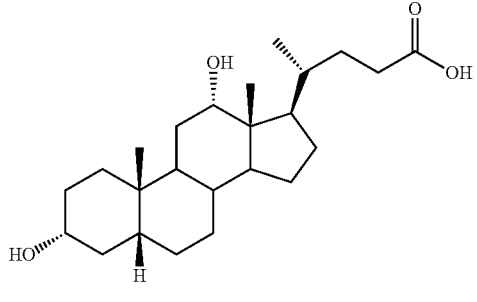

DCA

IV) optionally converting deoxycholic acid to a pharmaceutically acceptable salt thereof, wherein $R_1$ is $COOR_2$, $CH_2OH$, $CH_2OP$, $CH_2X$, $CH_2CHO$, $CH_2$—$CH_2$—$OH$, $CH_2$—$CH_2OP$, or $CH_2$—$CH_2X$ or $CH_2$—$CH_2$—$CHO$;

$R_2$ is H or a linear or branched $C_1$-$C_6$-alkyl group;

P is an alcohol protection group;

$R_3$ either P or $R_2$; and

X is a halogen atom.

L. The process according to embodiment K, wherein INT 3 is provided from INT 2 as defined in step IVa) of embodiment A.

M. The process according to embodiment L, wherein INT 2 is provided from INT 1 as defined in step III) of embodiment A.

N. The process according to embodiment M, wherein INT 1 is obtained from SM as defined in step II) of embodiment A.

O. The process according to embodiment K, comprising the following steps:

i) providing a compound of the general formula Int A3:

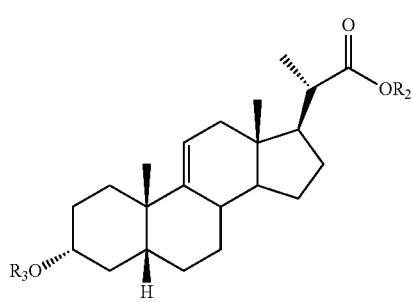

Int A3 ii) oxidising the intermediate of the general formula Int A3 into an intermediate of the general formula Int A5:

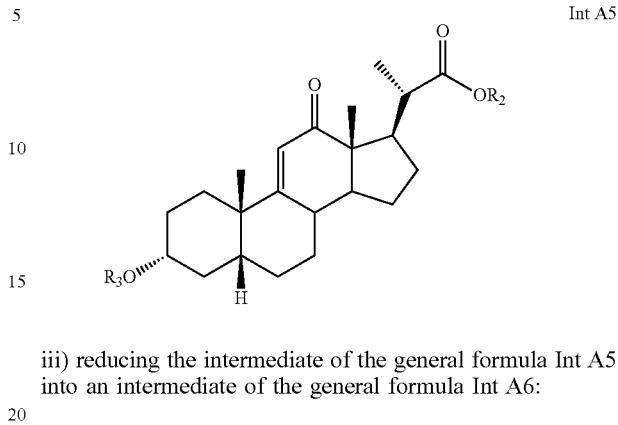

Int A5 iii) reducing the intermediate of the general formula Int A5 into an intermediate of the general formula Int A6:

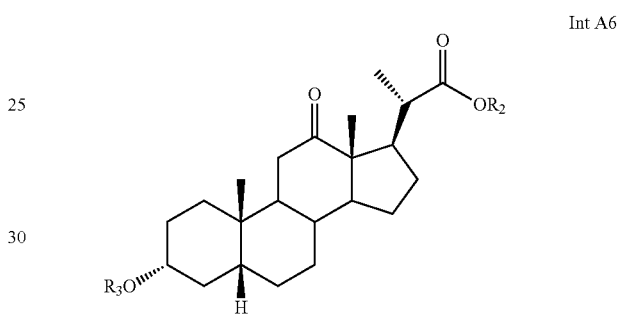

Int A6 iv) reducing the intermediate of the general formula Int A6 into an intermediate of the general formula Int A7:

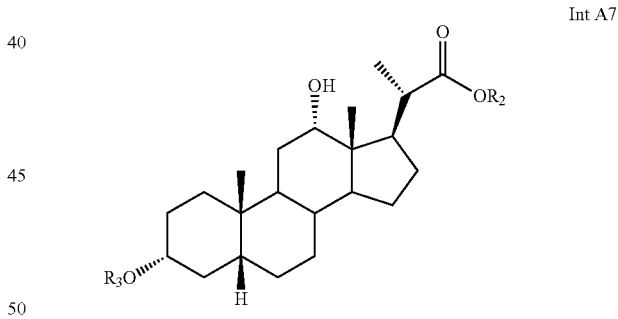

Int A7 v) reducing the compound of the general formula Int A7 into an intermediate of the general formula Int A8:

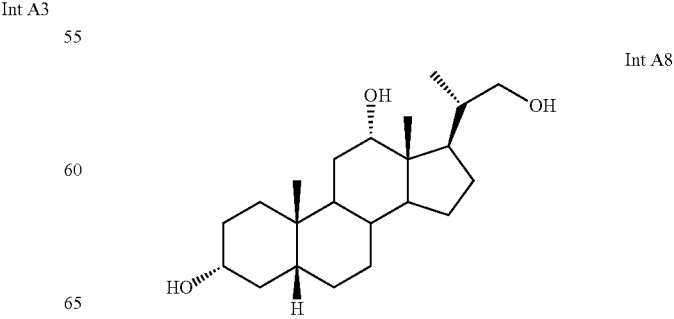

Int A8 vi) elongating the carbon chain of the compound of the general formula Int A8 to obtain deoxycholic acid (DCA):

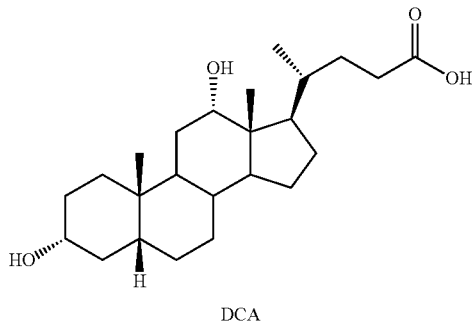

DCA vii) optionally converting deoxycholic acid to a pharmaceutically acceptable salt thereof, wherein $R_2$ is H or a linear or branched $C_1$-$C_6$-alkyl group;

$R_3$ is H, $R_2$ or an alcohol protection group.

P. The process according to embodiment O, wherein INT A3 is provided from INT A2 as defined in step iv) of embodiment B.

Q. The process according to embodiment P, wherein INT A2 is provided from INT A1 as defined in step iii) of embodiment B.

R. The process according to embodiment Q, wherein INT A1 is provided from SM-a as defined in step ii) of embodiment B.

S. The process according to any of embodiments K-R, wherein $R_2$ and $R_3$ are a defined in any of embodiments B-J.

T. A compound of the general formula I

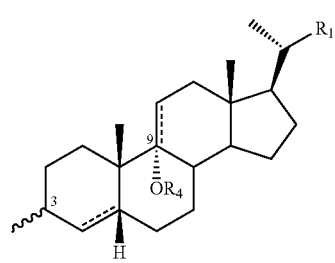

I wherein $R_1$ is $COOR_2$, $CH_2OH$, $CH_2OP$, $CH_2X$, $CH_2CHO$, $CH_2$—$CH_2$—$OH$, $CH_2$—$CH_2OP$, $CH_2$—$CH_2X$ or $CH_2$—$CH_2$—$CHO$;

$R_2$ is H or a linear or branched $C_1$-$C_6$-alkyl group;

P is an alcohol protection group;

X is a halogen atom;

------ is either a C—C bond or a C=C bond;

∿∿∿ is either =O or ⋯⋯OR$_3$ where $R_3$ is either P or $R_2$;

$OR_4$ is either OH or $R_4$ is the $C_3$ carbon in the A ring; and with the proviso that formula I is not

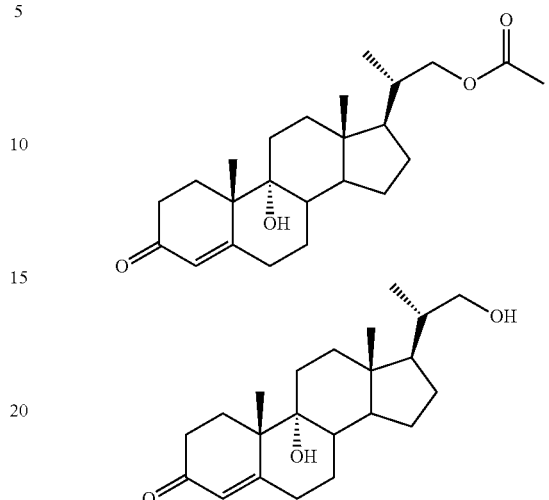

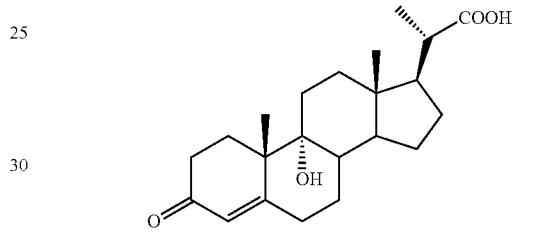

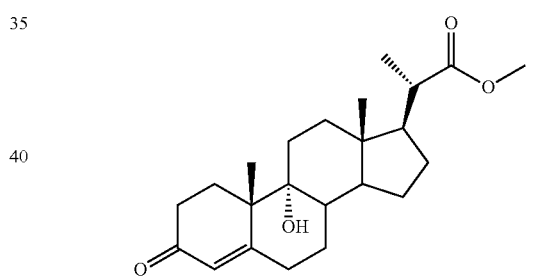

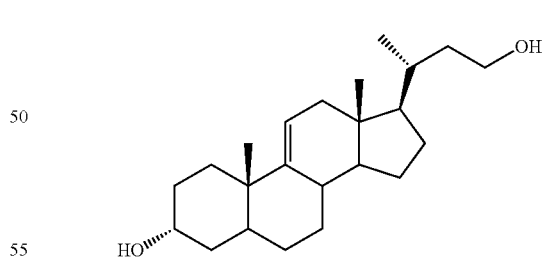

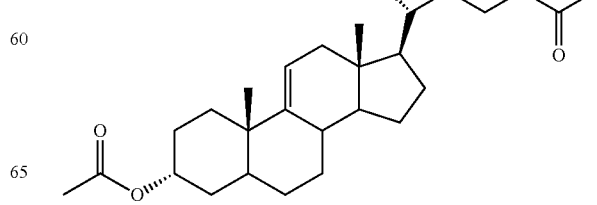

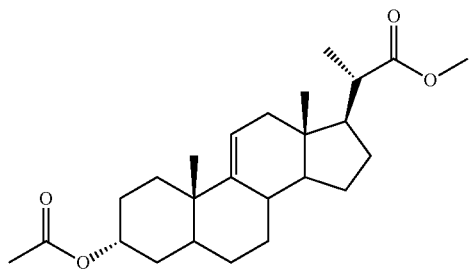 [SMILES: COC(=O)[C@@H](C)[C@H]1CCC2C3CCC4C[C@H](OC(C)=O)CC[C@]4(C)C3=CC[C@@]21C]

T1. The compound of embodiment T, wherein $R_1$ is $COOR_2$, $CH_2OP$, $CH_2X$, $CH_2CHO$, $CH_2$—$CH_2$—$OH$, $CH_2$—$CH_2OP$ or $CH_2$—$CH_2X$;

P is an alcohol protection group with the proviso that P is not Ac or Pv;

with the proviso that formula I is not

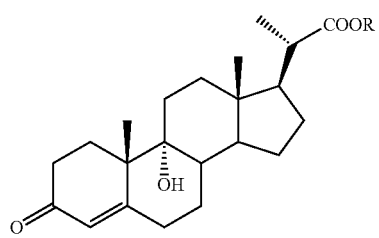

Wherein R is H or Me

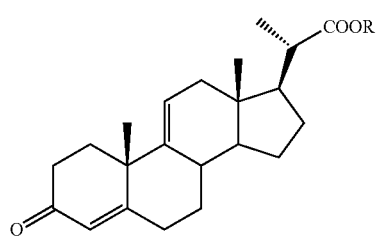

Wherein R is H or Me

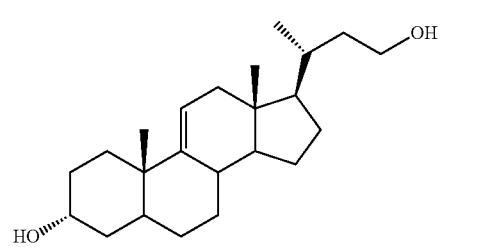

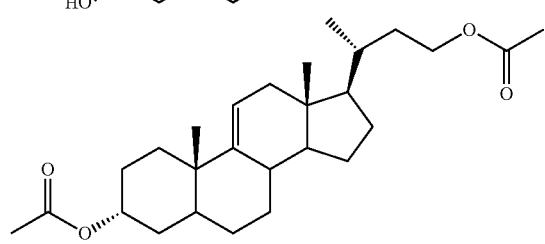

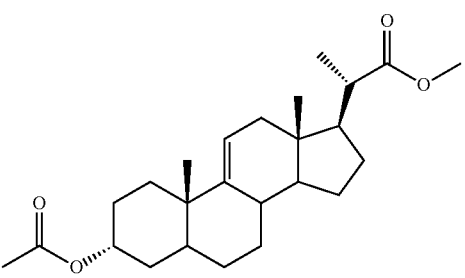

U. The compound according to embodiment T or T1 having the general formula SM

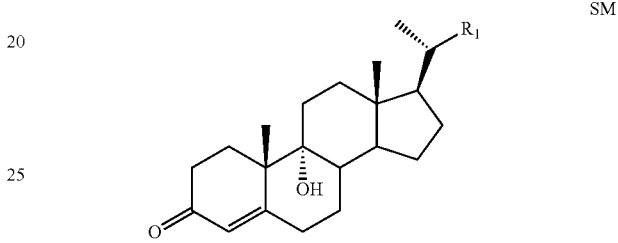

wherein $R_1$ is $COOR_2$, $CH_2OP$, $CH_2X$, $CH_2CHO$, $CH_2$—$CH_2$—$OH$, $CH_2$—$CH_2OP$, or $CH_2$—$CH_2X$ $R_2$ is a linear or branched $C_1$-$C_6$-alkyl group with the proviso that $R_2$ is not $CH_3$;

P is an alcohol protection group with the proviso that P is not Ac; and

X is a halogen atom.

V. The compound according to embodiment T or T1 having the general formula INT 1

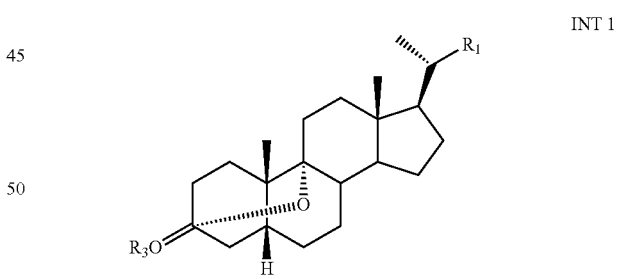

wherein $R_1$ is $COOR_2$, $CH_2OH$, $CH_2OP$, $CH_2X$, $CH_2CHO$, $CH_2$—$CH_2$—$OH$, $CH_2$—$CH_2OP$, $CH_2$—$CH_2X$ or $CH_2$—$CH_2$—$CHO$;

$R_2$ is H or a linear or branched $C_1$-$C_6$-alkyl group;

P is an alcohol protection group;

$R_3$ is either P or $R_2$; and

X is a halogen atom.

W. The compound according to embodiment T or T1 having the general formula INT 2

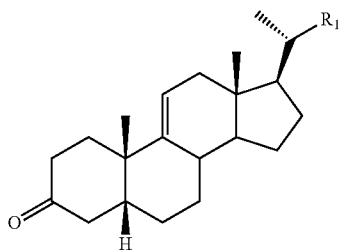

INT 2 wherein
$R_1$ is $COOR_2$, $CH_2OP$, $CH_2X$, $CH_2CHO$, $CH_2-CH_2-OH$, $CH_2-CH_2OP$ or $CH_2-CH_2X$;
$R_2$ is H or a linear or branched $C_1$-$C_6$-alkyl group;
P is an alcohol protection group; and
X is a halogen atom.

X. The compound according to embodiment T or T1 having the general formula INT 3

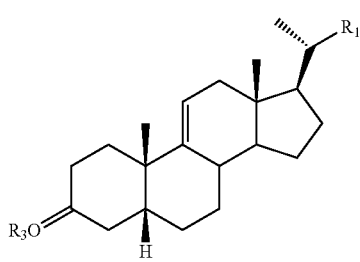

INT 3 wherein
$R_1$ is $COOR_2$, $CH_2OP$, $CH_2X$, $CH_2CHO$, $CH_2-CH_2-OH$, $CH_2-CH_2OP$ or $CH_2-CH_2X$;
$R_2$ is H or a linear or branched $C_1$-$C_6$-alkyl group;
P is an alcohol protection group;
$R_3$ is either P or $R_2$; and
X is a halogen atom.

Y. The compound according to any of embodiments U-X, wherein $R_1$ is $COOR_2$, $CH_2OP$ or $CH_2X$, where
$R_2$ is H or a linear or branched $C_1$-$C_6$-alkyl group;
P is an alcohol protection group;
$R_3$ is either P or $R_2$; and
X is a halogen atom.

Z. The compound according to any of embodiments U-Y, wherein $R_2$ is selected from the group consisting of methyl, ethyl, n-propyl and isopropyl.

AA. The compound according to embodiment Z, wherein $R_2$ is methyl or ethyl.

AB. The compound according to embodiment AA, wherein $R_2$ is methyl.

AC. The compound according to embodiment AA, wherein $R_2$ is ethyl.

AD. The compound according to any of embodiments U-Y, wherein $R_2$ is H.

AE. The compound according to any of embodiments U-Y, wherein X is selected from the group consisting of Cl, Br and I.

AF. The compound according to embodiment AE, wherein X is Br.

AG. The compound according to any of embodiments U-Y, wherein P is selected from the group consisting of trimethylsilyl ether (TMS), triethylsilyl ether (TES), triisopropylsilyl ether (TIPS), tert-butyldimethylsilyl ether (TBS, TBDMS), tert-butyldiphenylsilyl ether (TBDPS), acetyl (Ac, $COCH_3$), benzoyl (Bz), benzyl ether (Bn), 4-methoxybenzyl ether (PMB), 2-naphthylmethyl ether (Nap), methoxymethyl acetal (MOM), 2-methoxyethoxy-methyl ether (MEM), ethoxyethyl acetal (EE), methoxypropyl acetal (MOP), benzyloxymethyl acetal (BOM), tetrahydropyranyl acetal (THP), 2,2,2-trichloro-ethyl carbonate (Troc), methyl ether, dimethoxytrityl (DMT), methoxytrityl (MMT), methylthiomethyl ether, pivaloyl (Piv), tetrahydropyranyl (THP), triphenylmethyl (trityl, Tr), and tosyl (Ts).

AH. The compound according to embodiment AG, wherein P is selected from the group consisting of Ac, TBDMS and Ts.

AI. The compound according to any of embodiments U-AH, wherein $R_3$ is H.

AJ. The compound according to any of embodiments U-AH, wherein $R_3$ is $R_2$, and $R_2$ is as defined in any of embodiments Z-AC.

AK. The compound according to any of embodiments U-AH, wherein $R_3$ is P, and P is as defined in embodiment AG or AH.

AL. The compound according to embodiment AK, wherein $R_3$ is Ac.

AM. Use of a compound of the general formula I

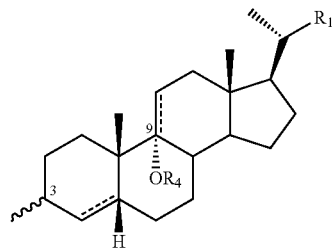

I wherein
$R_1$ is $COOR_2$, $CH_2OH$, $CH_2OP$, $CH_2X$, $CH_2CHO$, $CH_2-CH_2-OH$, $CH_2-CH_2OP$, $CH_2-CH_2X$ or $CH_2-CH_2-CHO$;
$R_2$ is H or a linear or branched $C_1$-$C_6$-alkyl group;
P is an alcohol protection group;
X is a halogen atom;
===== either a C—C bond or a C=C bond;
∿∿∿ is either =O or ⫶⫶⫶ $OR_3$ where $R_3$ is either P or $R_2$; and
$OR_4$ is either OH or $R_4$ is the $C_3$ carbon in the A ring;

for the preparation of deoxycholic acid (DCA), cholic acid, glycocholic acid, taurocholic acid, or a pharmaceutically acceptable salt thereof.

AN. Use according to embodiment AM, wherein the compound of the general formula I is as defined in any of embodiments U-AL.

The invention claimed is:

1. A method of making deoxycholic acid or a pharmaceutically acceptable salt thereof of formula (DCA)

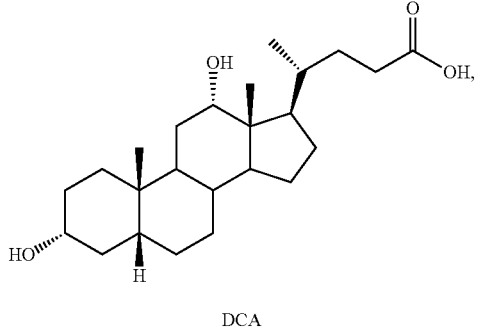 [SMILES: C[C@H](CCC(=O)O)[C@H]1CCC2C3CC[C@@H]4C[C@H](O)CC[C@]4(C)C3C[C@H](O)[C@@]21C]

DCA said method comprising:
 providing a compound of formula Int A8:

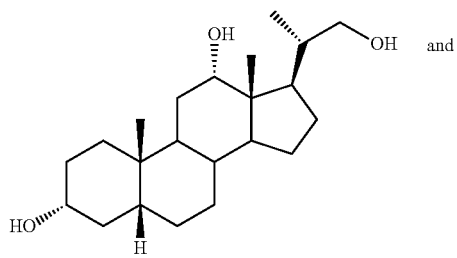

Int A8 converting the primary alcohol in the formula Int A8 into a leaving group (X) to obtain an intermediate of formula Int A9:

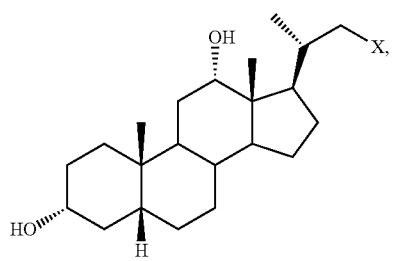

Int A9 wherein X is halogen, O-tosyl, or OP, wherein P is an alcohol protecting group; and
 elongating the carbon chain of the compound of the formula Int A9 to obtain DCA:

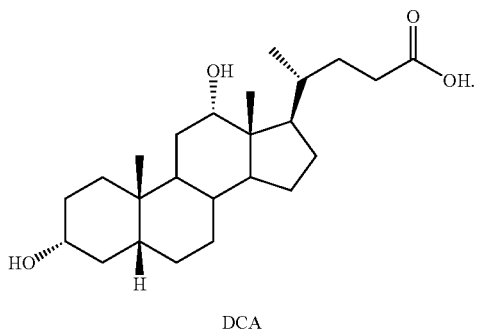 [SMILES: C[C@H](CCC(=O)O)[C@H]1CCC2C3CC[C@@H]4C[C@H](O)CC[C@]4(C)C3C[C@H](O)[C@@]21C]

DCA

2. The method according to claim 1, wherein said providing a compound of formula Int A8 comprises:
 providing a compound of formula Int A7:

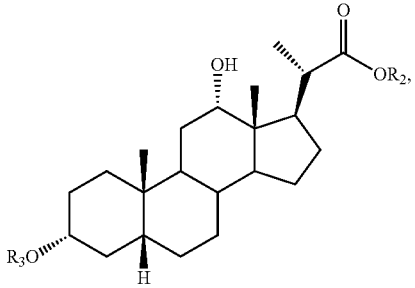

Int A7 wherein
 $R_2$ is H or a linear or branched $C_1$-$C_6$ alkyl group;
 $R_3$ is H, $R_2$, or an alcohol protection group; and
 reducing the compound of formula Int A7 to the compound of formula Int A8.

3. The method according to claim 2, wherein said providing a compound of formula Int A7 comprises:
 providing a compound of formula Int A6:

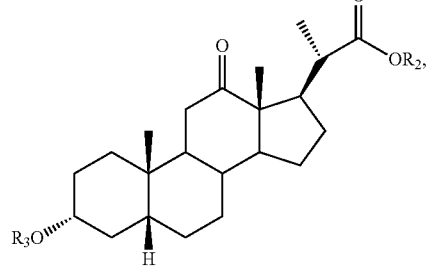

Int A6 wherein
 $R_2$ is H or a linear or branched $C_1$-$C_6$ alkyl group;
 $R_3$ is H, $R_2$, or an alcohol protection group; and
 converting reducing the compound of formula Int A6 to the compound of formula Int A7.

4. The method according to claim 3, wherein said providing a compound of formula Int A6 comprises:
providing a compound of formula Int A5:

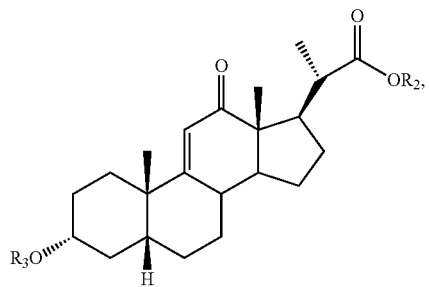

Int A5 wherein
$R_2$ is H or a linear or branched $C_1$-$C_6$ alkyl group;
$R_3$ is H, $R_2$, or an alcohol protection group; and
reducing the compound of formula Int A5 to the compound of formula Int A6.

5. The method according to claim 4, wherein said providing a compound of formula Int A5 comprises:
providing a compound of formula Int A3:

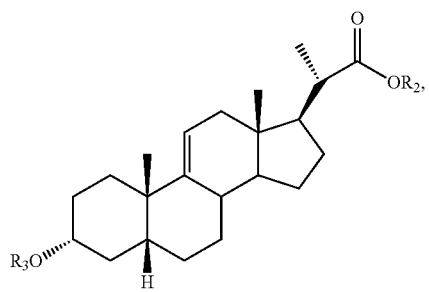

Int A3 wherein
$R_2$ is H or a linear or branched $C_1$-$C_6$ alkyl group;
$R_3$ is H, $R_2$, or an alcohol protection group; and
oxidizing the compound of formula Int A3 to the compound of formula Int A5.

6. The method according to claim 5, wherein said providing a compound of formula Int A3 comprises:
providing a compound of formula Int A2:

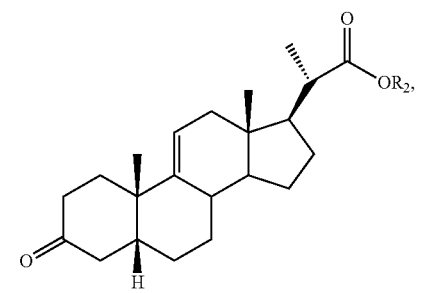

Int A2 wherein
$R_2$ is H or a linear or branched $C_1$-$C_6$ alkyl group; and
reducing the compound of formula Int A2 to the compound of formula Int A3.

7. The method according to claim 6, wherein said providing a compound of formula Int A2 comprises:
providing a compound of formula Int A1:

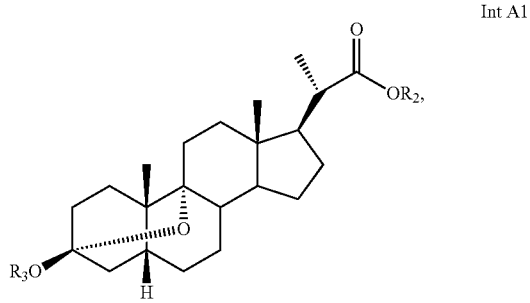

Int A1 wherein
$R_2$ is H or a linear or branched $C_1$-$C_6$ alkyl group;
$R_3$ is H, $R_2$, or an alcohol protection group; and
oxidizing the compound of formula Int A1 to the compound of formula Int A2.

8. The method according to claim 7, wherein said providing a compound of formula Int A1 comprises:
providing a compound of formula SM-a:

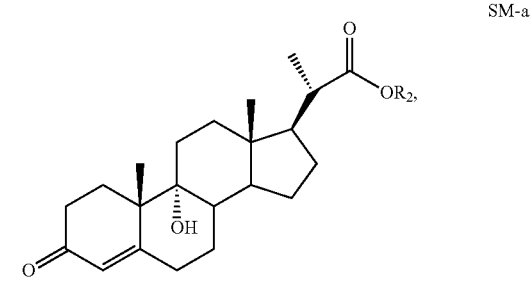

SM-a wherein
$R_2$ is H or a linear or branched $C_1$-$C_6$ alkyl group; and
reducing the compound of formula SM-a to the compound of formula of Int A1.

* * * * *

UNITED STATES PATENT AND TRADEMARK OFFICE
CERTIFICATE OF CORRECTION

PATENT NO. : 11,117,925 B2  
APPLICATION NO. : 15/579298  
DATED : September 14, 2021  
INVENTOR(S) : Antonio Lorente Bonde-Larsen et al.

It is certified that error appears in the above-identified patent and that said Letters Patent is hereby corrected as shown below:

In the Claims

Claim 3 Column 78, Line 66, delete "converting reducing" and insert --reducing--

Signed and Sealed this  
Thirtieth Day of November, 2021

Drew Hirshfeld  
*Performing the Functions and Duties of the*  
*Under Secretary of Commerce for Intellectual Property and*  
*Director of the United States Patent and Trademark Office*